United States Patent
Guedat

(10) Patent No.: US 10,709,677 B2
(45) Date of Patent: Jul. 14, 2020

(54) THERAPEUTIC USES OF BENZYLIDENEGUANIDINE DERIVATIVES FOR THE TREATMENT OF PROTEOPATHIES

(71) Applicant: InFlectis BioScience, Nantes (FR)

(72) Inventor: Philippe Guedat, Montenois (FR)

(73) Assignee: INFLECTIS BIOSCIENCE, Nantes (FR)

( * ) Notice: Subject to any disclaimer, the term of this patent is extended or adjusted under 35 U.S.C. 154(b) by 0 days.

(21) Appl. No.: 15/316,785

(22) PCT Filed: Jul. 2, 2015

(86) PCT No.: PCT/EP2015/065161
§ 371 (c)(1),
(2) Date: Dec. 6, 2016

(87) PCT Pub. No.: WO2016/001389
PCT Pub. Date: Jan. 7, 2016

(65) Prior Publication Data
US 2017/0151196 A1    Jun. 1, 2017

(30) Foreign Application Priority Data
Jul. 2, 2014  (EP) .................................. 14306075

(51) Int. Cl.
*A61K 31/155* (2006.01)
*A61K 31/44* (2006.01)
*A61K 31/53* (2006.01)

(52) U.S. Cl.
CPC ............ *A61K 31/155* (2013.01); *A61K 31/44* (2013.01); *A61K 31/53* (2013.01)

(58) Field of Classification Search
CPC ........ A61K 31/155; A61K 31/44; A61K 31/53
See application file for complete search history.

(56) References Cited

U.S. PATENT DOCUMENTS 3,541,217 A   11/1970 Marshall et al.
3,975,533 A    8/1976 Kodama et al.
(Continued)

FOREIGN PATENT DOCUMENTS

WO   WO-9303714   3/1993
WO   WO-0125192   4/2001

OTHER PUBLICATIONS

P. Tsaytler et al: "Selective Inhibition of a Regulatory Subunit of Protein Phosphatase 1 Restores Proteostasis", Science, vol. 332, No. 6025, Apr. 1, 2011(Apr. 1, 2011), pp. 91-94, XP055004683, ISSN: 0036-8075, DOI: 10.1126/science. 1201396 abstract.
(Continued)

*Primary Examiner* — San Ming R Hui
(74) *Attorney, Agent, or Firm* — B. Aaron Schulman, Esq.; Stits & Harbison, PLLC

(57) ABSTRACT

The present invention relates to novel uses of a compound of formula (I), or a tautomer and/or a pharmaceutically acceptable salt thereof, in treating a disorder associated with the PPP1R15A pathway and associated with protein misfolding stress and in particular with accumulation of misfolded proteins selected in the group of tauopathies, synucleinopathies, polyglutamine and polyalanine diseases, leukodystrophies, cystic fibrosis, multiple sclerosis, lysosomal storage disorders, amyloidosis diseases, inflammation, metabolic disorders, cardio-vascular disorders, osteoporosis, nervous system trauma, ischemia.

(Continued)

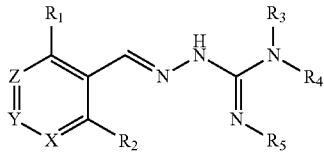

(I)

12 Claims, 8 Drawing Sheets

(56) References Cited

U.S. PATENT DOCUMENTS

| | | | |
|---|---|---|---|
| 3,982,020 A | 9/1976 | Houlihan et al. | |
| 7,932,422 B2 | 4/2011 | Bertolotti et al. | |
| 8,148,429 B2* | 4/2012 | Lundstedt | A61K 31/155 514/554 |
| 9,682,943 B2* | 6/2017 | Guedat | A61K 31/155 |
| 2009/0306430 A1 | 12/2009 | Becq et al. | |
| 2016/0015659 A1* | 1/2016 | Way | A61K 31/155 424/85.6 |
| 2016/0046589 A1 | 2/2016 | Guedat et al. | |
| 2017/0247344 A1 | 8/2017 | Guedat et al. | |

OTHER PUBLICATIONS

Vijayakumar N. Sonar et al: "(E)-1-[(2-Chlorophenyl)methyleneamino]guanidinium chloride", Acta Crystallographica Section E Structure Reports Online, vol. 63, No. 2, Jan. 31, 2007(Jan. 31, 2007), pp. 0974-0975, XP055136218, DOI: 10.1107/S1600536807002887 the whole document.

Tribouillard-Tanvier Deborah et al: "Antihypertensive drug guanabenz is active in vivo against both yeast and mammalian prions", PLOS One, Public Library of Science, US, vol. 3, No. 4, Jan. 1, 2008(Jan. 1, 2008), XP009156478, ISSN: 1932-6203, DOI: 10.1371/JOURNAL.PONE.0001981 the whole document.

I. Das et al: "Preventing proteostasis diseases by selective inhibition of a phosphatase regulatory subunit", Science, vol. 348, No. 6231, Apr. 10, 2015(Apr. 10, 2015), pp. 239-242, XP55207147, ISSN: 0036-8075, DOI: 10.1126/science.aaa4484 the whole document.

International Search Report for PCT/EP2015/065161, dated Aug. 31, 2015.

European Search Report for EP 14306075, completed Aug. 27, 2014.

Notification of Transmittal of the International Preliminary Report of Patentability for PCT/EP2015/065161, completed Jun. 10, 2016.

Notification of Transmittal of the International Search Report and the Written Opinion of the International Searching Authority, or the Declaration for PCT/EP2015/065161, dated Aug. 31, 2015.

* cited by examiner

THERAPEUTIC USES OF BENZYLIDENEGUANIDINE DERIVATIVES FOR THE TREATMENT OF PROTEOPATHIES

The present invention relates to compounds that have potential therapeutic applications in treating disorders associated with protein misfolding stress and in particular with an accumulation of misfolded proteins. In particular, the invention provides compounds that are capable of exhibiting a protective effect against cytotoxic endoplasmic reticulum (ER) stress.

BACKGROUND TO THE INVENTION

The compound 2-(2,6-dichlorobenzylidene)hydrazinecarboximidamide, also referred to as guanabenz, is an alpha agonist of the alpha-2 type that is used as an antihypertensive drug.

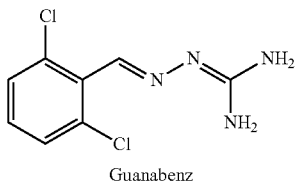

Guanabenz

Various derivatives of guanabenz have also been reported. For example, U.S. Pat. No. 3,982,020 (Sandoz, Inc.) discloses substituted benzylidene hydrazines and their use as hypoglycemic-antihyperglycemic agents, anti-obesity agents and anti-inflammatory agents. US 2004/0068017 (Bausch & Lomb Inc.) discloses substituted benzylidene hydrazines that are capable of increasing the activity of gelatinase A in ocular cells. The molecules have applications in the treatment of primary open angle glaucoma. WO 2008/061647 (Acure Pharma AB) discloses the use of N-(2-chloro-3,4,-dimethoxybenzylideneamino)guanidine as a VEGFR inhibitor and its associated applications in the treatment or prevention of undesired blood vessel formation during tumour growth and/or inflammatory conditions. WO 2005/031000 (Acadia Pharmaceuticals, Inc.) discloses substituted benzylidene hydrazines and their use in treating acute pain and chronic neuropathic pain. Finally, EP1908464 (CNRS) discloses guanabenz and chloroguanabenz and their use in the treatment of polyglutamine expansion associated diseases, including Huntington's disease.

More recently it has been reported that guanabenz has therapeutic potential in a number of other areas. Guanabenz, was recently noted to have anti-prion activity (D. Tribouillard-Tanvier et al., 2008 PLoS One 3, e1981). It has been reported that its activity in protecting against protein misfolding is surprisingly much broader and includes attenuating accumulation of mutant Huntingtin in cell-based assays (WO 2008/041133) and protection against the lethal effects of expression of misfolding prone Insulin Akita mutant in the endoplasmic reticulum (ER) of Min6 and INS-1 pancreatic beta-cells (Tsaytler et al., Science 2011 Vol. 332, 1 pp 91-94). WO2014/138298 and Way et al. (2015 Nature Communications 6:6532 DOI: 10.1038/ncomms7532) disclose guanabenz ant its use in the treatment of demyelinating disorder, such as multiple sclerosis.

Guanabenz has also been shown to promote survival of HeLa cells exposed to otherwise cytotoxic ER-stress induced by the N-glycosylation inhibitor tunicamycin, in a dose-dependent manner (Tsaytler et al., Science 2011). Quantitative assessment of cell viability revealed that guanabenz doubled the number of cells surviving ER stress with a median effective concentration of ~0.4 µM. Neither the α2-adrenergic receptor agonist clonidine, nor the α2-adrenergic receptor antagonist efaroxan protected cells from cytotoxic ER stress and efaroxan did not interfere with guanabenz's protective effect (Tsaytler et al., Science 2011). These observations demonstrate that guanabenz rescues cells from lethal ER stress by a mechanism independent of the α2-adrenergic receptor. Guanabenz protects cells from otherwise lethal accumulation of misfolded proteins by binding to a regulatory subunit of protein phosphatase 1, PPP1R15A (GADD34), selectively disrupting the stress-induced dephosphorylation of the α subunit of translation initiation factor 2 (eIF2α). Guanabenz sets the translation rates in stressed cells to a level manageable by available chaperones, thereby restoring protein homeostasis. It was reported that Guanabenz does not bind to the constitutive PPP1R15B (CReP) and therefore does not inhibit translation in non-stressed cells (Tsaytler et al., Science 2011).

Failure to maintain proteostasis in the ER by mounting an adequate unfolded protein response (UPR) is recognized as a contributing factor to many pathological conditions. Thus, the molecules described here, which inhibit eIF2α phosphatase to fine-tune protein synthesis, may be of therapeutic benefit to a large number of diseases caused protein misfolding stress and in particular with an accumulation of misfolded proteins.

The present invention seeks to provide alternative compounds based on a guanabenz core structure that have potential therapeutic applications in treating disorders associated with protein misfolding stress and in particular with an accumulation of misfolded proteins.

STATEMENT OF INVENTION

A first aspect of the invention relates to a compound of formula (I), or a pharmaceutically acceptable salt thereof,

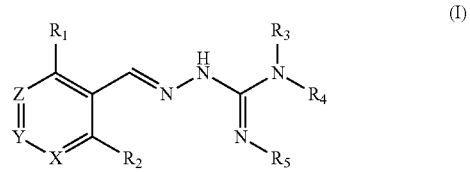

wherein:
$R_1$ is alkyl, O-alkyl, Cl, F or Br;
$R_2$ is H or F;
$R_3$ is selected from H and alkyl;
$R_4$ is selected from H and $C(O)R_6$;
$R_5$ is H;
or $R_4$ and $R_5$ are linked to form a 5 to 6 membered saturated or unsaturated heterocyclic group optionally comprising 1 or 2 heteroatoms such as N, in addition to the N atoms to which $R_4$ and $R_5$ are bound, and where said heterocyclic group is optionally substituted with one or more $R_{10}$ groups;
$R_6$ is selected from $R_7$, $OR_7$ and $NR_8R_9$;
$R_7$, $R_8$ and $R_9$ are each independently selected from alkyl, cycloalkyl, aralkyl, cycloalkenyl, heterocyclyl and aryl, each of which is optionally substituted with one or more $R_{10}$ groups;

each $R_{10}$ is independently selected from halogen, OH, =O, ON, COO-alkyl, aralkyl, $SO_2$-alkyl, $SO_2$-aryl, COOH, CO-alkyl, CO-aryl, $NH_2$, NH-alkyl, $N(alkyl)_2$, $CF_3$, alkyl and alkoxy;

X and Z are each independently $CR_{11}$, and Y is selected from $CR_{11}$ and N;

$R_{11}$ is H, alklyl or F;

for use in treating a proteopathy and/or a disorder associated with protein misfolding stress and in particular with an accumulation of misfolded proteins.

A second aspect of the invention relates to a compound of formula (I), or a pharmaceutically acceptable salt thereof,

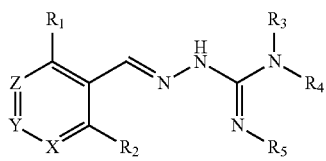

(I)

wherein:
$R_1$ is alkyl, O-alkyl, Cl, F or Br;
$R_2$ is H or F;
$R_3$ is selected from H and alkyl;
$R_4$ is selected from H and $C(O)R_6$;
$R_5$ is H;
or $R_4$ and $R_5$ are linked to form a 5 to 6 membered saturated or unsaturated heterocyclic group optionally comprising 1 or 2 heteroatoms such as N, in addition to the N atoms to which $R_4$ and $R_5$ are bound, and where said heterocyclic group is optionally substituted with one or more $R_{10}$ groups;
$R_6$ is selected from $R_7$, $OR_7$ and $NR_8R_9$;
$R_7$, $R_8$ and $R_9$ are each independently selected from alkyl, cycloalkyl, aralkyl, cycloalkenyl, heterocyclyl and aryl, each of which is optionally substituted with one or more $R_{10}$ groups;
each $R_{10}$ is independently selected from halogen, OH, =O, ON, COO-alkyl, aralkyl, $SO_2$-alkyl, $SO_2$-aryl, COOH, CO-alkyl, CO-aryl, $NH_2$, NH-alkyl, $N(alkyl)_2$, $CF_3$, alkyl and alkoxy;
X, Y and Z are each independently $CR_{11}$.
$R_{11}$ is H, alkyl or F;
for use in treating a proteopathy and/or a disorder associated with protein misfolding stress and in particular with an accumulation of misfolded proteins.

A third aspect of the invention relates to a compound of formula (I), or a pharmaceutically acceptable salt thereof,

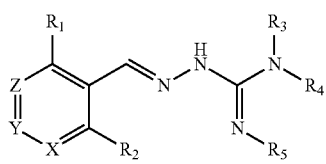

(I)

wherein:
R1 is Cl;
R2 is H;
R3 is selected from H and alkyl;
R4 is selected from H and C(O)R6;
R5 is H;
or $R_4$ and $R_5$ are linked to form a 5 to 6 membered saturated or unsaturated heterocyclic group optionally comprising 1 or 2 heteroatoms such as N, in addition to the N atoms to which $R_4$ and $R_5$ are bound, and where said heterocyclic group is optionally substituted with one or more $R_{10}$ groups;
R6 is selected from R7, OR7 and NR8R9;
R7, R8 and R9 are each independently selected from alkyl, cycloalkyl, aralkyl, cycloalkenyl, heterocyclyl and aryl, each of which is optionally substituted with one or more R10 groups;
each R10 is independently selected from halogen, OH, =O, CN, COO-alkyl, aralkyl, SO2-alkyl, SO2-aryl, COOH, CO-alkyl, CO-aryl, NH2, NH-alkyl, N(alkyl)2, CF3, alkyl and alkoxy;
X, Y and Z are each independently CR11;
R11 is H, alkyl, or F;
for use in treating a proteopathy and/or a disorder associated with protein misfolding stress and in particular with an accumulation of misfolded proteins.

A fourth aspect of the invention relates to a compound of formula (I), or a pharmaceutically acceptable salt thereof,

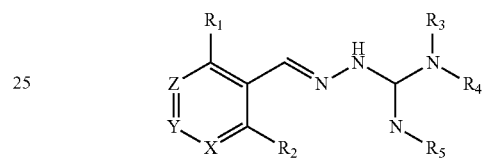

(I)

wherein:
R1 is alkyl, O-alkyl, Cl, F or Br;
R2 is H or F;
R3 is selected from H and alkyl;
R4 is selected from H and C(O)R6;
R5 is H;
or $R_4$ and $R_5$ are linked to form a 5 to 6 membered saturated or unsaturated heterocyclic group optionally comprising 1 or 2 heteroatoms such as N, in addition to the N atoms to which $R_4$ and $R_5$ are bound, and where said heterocyclic group is optionally substituted with one or more $R_{10}$ groups;
R6 is selected from R7, OR7 and NR8R9;
R7, R8 and R9 are each independently selected from alkyl, cycloalkyl, aralkyl, cycloalkenyl, heterocyclyl and aryl, each of which is optionally substituted with one or more R10 groups;
each R10 is independently selected from halogen, OH, =O, CN, COO-alkyl, aralkyl, SO2-alkyl, SO2-aryl, COOH, CO-alkyl, CO-aryl, NH2, NH-alkyl, N(alkyl)2, CF3, alkyl and alkoxy;
X and Z are each independently CR11, and Y is N;
R11 is H, alkyl or F;

Previous studies have indicated that the aryl group must be at least di-substituted in order for the compounds to exhibit useful pharmacological activity (see for example, D. Tribouillard-Tanvier et al., PLoS One 3, e1981 (2008) and EP1908464A, CNRS). However, contrary to the results of previous studies, the present Applicant has surprisingly found that mono-substituted aryl derivatives are also active.

Moreover, compounds of formula (I) as defined above advantageously exhibit no activity or low activity toward the adrenergic α2A receptor relative to prior art compounds such as Guanabenz. This loss in alpha-2 adrenergic activity renders the compounds therapeutically useful in the treatment of proteopathies and/or disorders associated with protein misfolding stress and in particular with an accumulation of misfolded proteins. The absence of alpha-2 adrenergic activity means that compounds of formula (I) can be administered at a dosage suitable to treat the aforementioned diseases, without any significant effect on blood pressure.

A further aspect of the invention relates to pharmaceutical compositions comprising a compound of formula (I) as described above, admixed with a suitable pharmaceutically acceptable diluent, excipient or carrier.

DETAILED DESCRIPTION

As used herein, the term "alkyl" includes both saturated straight chain and branched alkyl groups. Preferably, the alkyl group is a $C_{1-20}$ alkyl group, more preferably a $C_{1-15}$, more preferably still a $C_{1-12}$ alkyl group, more preferably still, a $C_{1-6}$ alkyl group, more preferably a $C_{1-3}$ alkyl group. Particularly preferred alkyl groups include, for example, methyl, ethyl, propyl, isopropyl, butyl, isobutyl, tert-butyl, pentyl and hexyl As used herein, the term "cycloalkyl" refers to a cyclic alkyl group. Preferably, the cycloalkyl group is a $C_{3-12}$ cycloalkyl group.

As used herein, the term "alkenyl" refers to a group containing one or more carbon-carbon double bonds, which may be branched or unbranched. Preferably the alkenyl group is a $C_{2-20}$ alkenyl group, more preferably a $C_{2-15}$ alkenyl group, more preferably still a $C_{2-12}$ alkenyl group, or preferably a $C_{2-6}$ alkenyl group, more preferably a $C_{2-3}$ alkenyl group. The term "cyclic alkenyl" is to be construed accordingly.

As used herein, the term "aryl" refers to a $C_{6-12}$ aromatic group. Typical examples include phenyl and naphthyl etc.

As used herein, the term "heterocycle" (also referred to herein as "heterocyclyl" and "heterocyclic") refers to 4 to 12 membered, preferably 4 to 12 membered saturated, unsaturated or partially unsaturated cyclic group containing one or more heteroatoms selected from N, O and S, and which optionally further contains one or more CO groups. The term "heterocycle" encompasses both heteroaryl groups and heterocycloalkyl groups as defined below.

As used herein, the term "heteroaryl" refers to a 4 to 12 membered aromatic, which comprises one or more heteroatoms. Preferably, the heteroaryl group is a 4 to 12 membered aromatic group comprising one or more heteroatoms selected from N, O and S. Suitable heteroaryl groups include pyrrole, pyrazole, pyrimidine, pyrazine, pyridine, quinoline, thiophene, 1,2,3-triazole, 1,2,4-triazole, thiazole, oxazole, iso-thiazole, iso-oxazole, imidazole, furan and the like.

As used herein, the term "heterocycloalkyl" refers to a 4 to 12 membered cyclic aliphatic group which contains one or more heteroatoms. Preferred heterocycloalkyl groups include piperidinyl, pyrrolidinyl, piperazinyl, thiomorpholinyl and morpholinyl. More preferably, the heterocycloalkyl group is selected from N-piperidinyl, N-pyrrolidinyl, N-piperazinyl, N-thiomorpholinyl and N-morpholinyl.

As used herein, the term "aralkyl" includes, but is not limited to, a group having both aryl and alkyl functionalities. By way of example, the term includes groups in which one of the hydrogen atoms of the alkyl group is replaced by an aryl group, e.g. a phenyl group. Typical aralkyl groups include benzyl, phenethyl and the like.

In one preferred embodiment, $R_1$ is Cl, Br, Me or F, more preferably, Cl.

In one preferred embodiment, $R_2$ is H.
In one preferred embodiment, Y is $CR_{11}$.
In another preferred embodiment, Y is N.
In one preferred embodiment, $R_3$ and $R_4$ are both H.
In one preferred embodiment, $R_3$ is H and $R_4$ is $C(O)R_6$.

In one preferred embodiment, $R_6$ is alkyl or alkoxy, more preferably, Me or OMe.

In one preferred embodiment, $R_4$ and $R_5$ are linked to form a 5 to 6 membered saturated or unsaturated heterocyclic group optionally comprising 1 or 2 heteroatoms such as N, in addition to the N atoms to which $R_4$ and $R_5$ are bound, and where said heterocyclic group is optionally substituted with one or more $R_{10}$ groups;

In one preferred embodiment, said compound is of formula (Ia), or a pharmaceutically acceptable salt thereof,

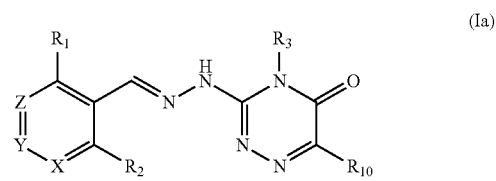

(Ia)

wherein $R_1$, $R_2$, $R_3$ and $R_{10}$ are as defined above.

In one especially preferred embodiment, the compound of formula (I) is selected from the following:

Compound 1

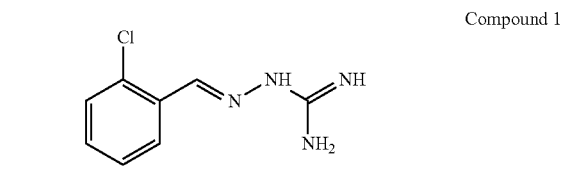

Compound 2

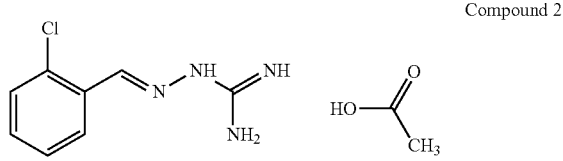

Compound 3

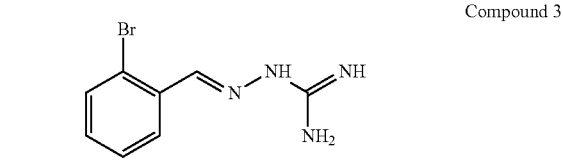

Compound 4

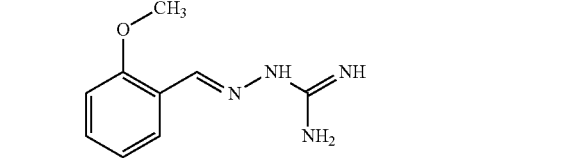

Compound 5

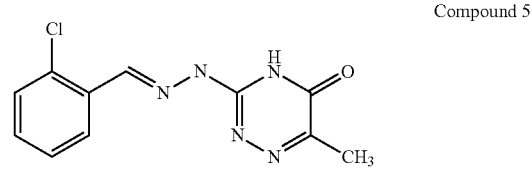

Compound 6

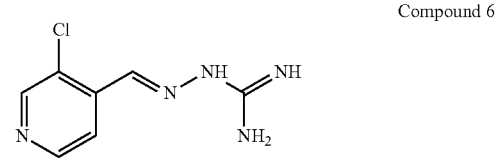

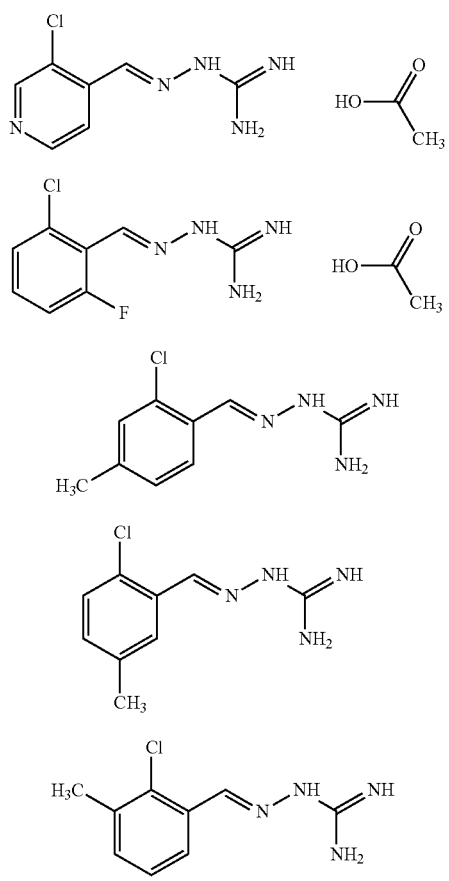

and pharmaceutically acceptable salts thereof.

In a first preferred embodiment, the compound of formula (I) is selected from Compound 1 i.e. 1-[[(2-chlorophenyl)methylidene]amino]-guanidine and Compound 2, i.e. 1-[[(2-chlorophenyl) methylidene]amino]-guanidine acetate, as set out above. In a second preferred embodiment, the compound of formula (I) is selected from Compound 8 as set out above.

In a third preferred embodiment, the compound of formula (I) is selected from Compound 6 and Compound 7, as set out above.

Therapeutic Applications

The compounds of formula (I) have potential therapeutic applications in treating proteopathies and/or disorders associated with accumulation of misfolded and/or unfolded proteins. In particular, compounds of formula (I) have a protective effect against cytotoxic endoplasmic reticulum (ER) stress and age related disorders.

Another aspect of the invention relates to the use of a compound of formula (I) as defined above in the preparation of a medicament for treating a disorder associated with protein misfolding stress and in particular with an accumulation of misfolded proteins.

Another aspect of the invention relates to the use of a compound of formula (I) as defined above in the preparation of a medicament for treating diseases where accumulation of misfolded and/or unfolded proteins is involved in the mode of action (Brown et al, 2012, Frontiers in Physiology, 3, Article 263).

Another aspect of the invention relates to the use of a compound of formula (I) as defined above in the preparation of a medicament for treating a proteopathy. The proteopathies refer to a class of diseases in which certain proteins become structurally abnormal, and thereby disrupt the function of cells, tissues and organs of the body. Often the proteins fail to fold into their normal conformation, and in this misfolded and/or unfolded state, the proteins can become toxic in some way (a gain of toxic function) or they can lose their normal function or they can have a reduce biological activity. The proteopathies, also known as proteinopathies, protein conformational disorders, or protein misfolding diseases, include many diseases such diseases as Alzheimer's disease, Parkinson's disease, prion disease, type 2 diabetes, amyloidosis, and a wide range of other disorders (see non limiting examples below).

As used herein the terms "proteinopathies, proteopathies, protein conformational disorders, protein misfolding diseases, diseases associated with protein misfolding stress, diseases associated with an accumulation of misfolded protein, diseases associated with a cytotoxic ER stress, UPR related diseases associated with have the same meaning and refer to diseases wherein certain protein become structurally abnormal and thereby disrupt the cellular homeostasis.

As used herein the terms "misfolded protein" and "unfolded protein" has the same meaning and refer to protein that fail to fold into their normal conformation.

As used herein the phrase "preparation of a medicament" includes the use of one or more of the above described compounds directly as the medicament in addition to its use in a screening programme for further active agents or in any stage of the manufacture of such a medicament.

Yet another aspect of the invention relates to a method of treating a proteinopathy and/or a disorder associated with protein misfolding stress and/or with a cytotoxic ER stress and in particular with an accumulation of misfolded proteins in a subject in need thereof, said method comprising administering a therapeutically effective amount of a compound of formula (I) as defined above to said subject.

The term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

Herein, the term "treating" includes abrogating, substantially inhibiting, slowing or reversing the progression of a disease or disorder, substantially ameliorating clinical symptoms of a disease or disorder or substantially preventing the appearance of clinical symptoms of a disease or disorder.

As used herein, the term «disease», «disorder», «conditions» has the same meaning. The disease is associated with an ER stress response activity and/or is associated with protein misfolding stress and in particular with an accumulation of misfolded proteins.

The term "therapeutically effective amount" refers to that amount of the compound being administered which will relieve to some extent one or more of the symptoms of the disease or disorder being treated.

In another embodiment, the invention relates to a compound of formula (I) as defined above for use in treating UPR disorders. The unfolded protein response (UPR) is a component of the cellular defense system against misfolded proteins that adapts folding in the endoplasmic reticulum (ER) to changing conditions. The UPR is activated in response to an accumulation of unfolded or misfolded proteins in the lumen of the endoplasmic reticulum. In this scenario, the UPR has two primary aims: (i) to restore normal function of the cell by halting protein translation, and (ii) to activate the signaling pathways that lead to the increased production of molecular chaperones involved in protein folding. If these objectives are not achieved within a certain time frame, or the disruption is prolonged, the UPR aims towards apoptosis. Upstream components of the UPR are the ER-resident trans-membrane proteins IRE1, ATF6, and PERK, which sense folding defects to reprogram transcription and translation in a concerted manner and restore proteostasis. Activated IRE1 and ATF6 increase the transcription of genes involved in ER folding, such as those encoding the chaperones BiP and GRP94. Activated PERK attenuates global protein synthesis by phosphorylating the subunit of translation initiation factor 2 (eIF2α) on Ser51 while promoting translation of the transcription factor ATF4. The latter controls expression of CHOP, another transcription factor, which in turn promotes expression of PPP1R15A/GADD34. PPP1R15A, an effector of a negative feedback loop that terminates UPR signaling, recruits a catalytic subunit of protein phosphatase 1 (PP1c) to dephosphorylate eIF2α, allowing protein synthesis to resume. UPR failure contributes to many pathological conditions that might be corrected by adequate boost of this adaptive response. Selective inhibitors of the stressed-induced eIF2α phosphatase PPP1R15A-PP1 delays eIF2α dephosphorylation and consequently protein synthesis selectively in stressed cells, without affecting protein synthesis in unstressed cells. This prolongs the beneficial effects of the UPR. A transient reduction of protein synthesis is beneficial to stressed cells because decreasing the flux of proteins synthetized increases the availability of chaperones and thus protects from misfolding stress (Tsaytler et al., Science 2011). Non-selective inhibitors of the 2 eIF2α phosphatases might have undesirable effects, as persistent translation inhibition is deleterious. Indeed, genetic ablation of both PPP1R15A and PPP1R15B results in early embryonic lethality in mice indicating that inhibition of the two eIF2α phosphatases PPP1R15A-PP1 and PPP1R15B-PP1 is deleterious in an organismal context. In contrast, genetic ablation of PPP1R15A has no harmful consequence in mice (Harding et al., 2009, Proc Natl Acad Sci USA, 106, 1832-1837). Furthermore, specific inhibitors of PPP1R15A are predicted to be inert in unstressed cells, as the PPP1R15A is not expressed in absence of stress. Thus, selective PPP1R15A inhibitors are predicted to be safe. Non-selective inhibitors of the two eIF2α phosphatases may also be useful to treat protein misfolding diseases, when used at doses that result in only a partial inhibition of the phosphatases.

Cytoprotection against ER stress can be measured by a suitable assay. For example, cytoprotection can be measured in HeLa cells in which ER stress is elicited by the addition of media containing tunicamycin, a mixture of homologous nucleoside antibiotics that inhibits the UDP-HexNAc: polyprenol-P HexNAc-1-P family of enzymes and is used to induce unfolded protein response. Cell viability can be detected in the presence and absence of inhibitor compounds after a set period of time, by measuring the reduction of WST-8 into formazan using a standard cell viability kit (such as Cell Viability Counting Kit-8 from Dojindo). The man skilled in the art may use other class of tetrazolium compounds such as MTT, MTS, XTT. Cytoprotection from ER stress is measured in terms of the percentage increase in viable cells (relative to control) after ER stress. Alternative cell viability assays may be used such as luminogenic ATP assay. Further details of a suitable assay are set forth in the accompanying Examples section.

In one preferred embodiment, the compound of formula (I) is capable of prolonging the protective effect of the UPR relative to the control (i.e. in the absence of inhibitor compound) by at least 10%, at least 20%, more preferably, at least 30%, even more preferably, at least 40%, at least 50%, at least 60%, at least 70%, at least 80%, more preferably still, at least 90%.

The compounds of formula (I) are inhibitors of PPP1R15A-PP1 interaction which induce a protective effect. Preferably, the compound exhibits a protective effect with $EC_{50}$ of less than about 10 µM, even more preferably, less than about 5 µM, more preferably still, less than about 1 µM. The compound should preferably be devoid of alpha2 adrenergic activity. Thus, in one preferred embodiment the compound does not exhibit any activity in a functional alpha-2-adrenergic assay.

Certain compounds of formula (I) selectively inhibit PPP1R15A-PP1, and thus prolong the protective effect of the UPR, thereby rescuing cells from protein misfolding stress. Inhibitors of PPP1R15A-PP1 described in the present invention therefore have therapeutic applications in the treatment of a variety of diseases associated with protein misfolding stress and in particular with an accumulation of misfolded proteins and/or proteinopathies.

In one embodiment, the compound of formula (I) is capable of inhibiting PPP1R15A and PPP1R15B. In highly preferred embodiment, the compound of formula (I) is capable of selectively inhibiting PPP1R15A over PPP1R15B.

In one embodiment, the invention relates to a compound of formula (I) as defined above for use in treating a disorder associated with the eIF2α phosphorylation pathway where accumulation of misfolded proteins is involved in the mode of action. Preferably, the disorder is a PPP1R15A-related disease. Examples of such disorders include protein misfolding diseases and/or proteinopathies.

In another embodiment, the invention relates to a compound of formula (I) as defined above for use in treating a disorder caused by, associated with or accompanied by eIF2α phosphorylation and/or PPP1R15A activity where accumulation of misfolded proteins is involved in the mode of action.

As used herein, "PPP1R15A related disease or disorder" refers to a disease or disorder characterized by abnormal PPP1R15A activity where accumulation of misfolded proteins is involved in the mode of action. Abnormal activity refers to: (i) PPP1R15A expression in cells which normally do not express PPP1R15A; (ii) increased PPP1R15A expression; or, (iii) increased PPP1R15A activity.

In another embodiment, the invention relates to a method of treating a mammal having a disease state alleviated by the inhibition of PP1R15A, where accumulation of misfolded proteins is involved in the mode of action, wherein the method comprises administering to a mammal a therapeutically effective amount of a compound of formula (I) as defined above.

In another embodiment, the invention relates to a PPP1R15A inhibitor of formula (I) or a pharmaceutical acceptable salt thereof for the use in treating disorders associated with protein misfolding stress and in particular with an accumulation of misfolded proteins and/or UPR disorders, wherein said compound has no or reduced adrenergic alpha 2 agonist activity in comparison with Guanabenz.

In another embodiment, the invention relates to a PPP1R15A inhibitor of formula (I) or a pharmaceutical acceptable salt thereof for the use in treating disorders associated with protein misfolding stress and in particular with an accumulation of misfolded proteins and/or UPR disorders, wherein said compound does not inhibit protein translation in non-stressed cells expressing PPP1R15B.

In another embodiment, the invention relates to a method of treating a disorder characterized by ER stress response activity with an accumulation of misfolded proteins, the method comprising administering to a patient a therapeutically effective amount of at least one compound of formula (I) wherein said compound modulates ER stress response.

In another embodiment, the invention relates to PPP1R15A inhibitor of formula (I) or a pharmaceutical acceptable salt thereof for the use in treating proteopathies and/or disorders associated with protein misfolding stress and in particular with an accumulation of misfolded proteins and/or UPR disorders, wherein said compound has a selectivity towards PPP1R15A-PP1 holophosphatase, having but no or reduced activity towards PPP1R15B-PP1 holophosphatase, and wherein the ratio (activity towards PPP1R15A-PP1 holophosphatase/activity towards PPP1R15B-PP1) for said compound is at least equal or superior to the ratio (activity towards PPP1R15A-PP1 holophosphatase/activity towards PPP1R15B-PP1) for Guanabenz.

In another embodiment, the invention relates to a PPP1R15A inhibitor of formula (I) or a pharmaceutical acceptable salt thereof for the use in treating proteopathies and/or disorders associated with protein misfolding stress and in particular with an accumulation of misfolded proteins and/or UPR disorders:
  wherein said compound has an activity towards PPP1R15A-PP1 holophosphatase but no or reduced activity towards PPP1R15B-PP1 holophosphatase, and;
  wherein the ratio (activity towards PPP1R15A-PP1 holophosphatase/activity towards PPP1R15B-PP1) for said compound is at least equal or superior to the ratio (activity towards PPP1R15A-PP1 holophosphatase/activity towards PPP1R15B-PP1) for Guanabenz; and
  wherein said compound has no or reduced adrenergic alpha 2 agonist activity in comparison with Guanabenz.

The disease or disorders according to the invention is:
  (i) associated with an ER stress response activity; and/or
  (ii) protein misfolding stress and in particular with an accumulation of misfolded and/or unfolded proteins; and/or
  (iii) an UPR disorder; and/or
  (iv) PPP1R15A related disease; and/or
  (v) A proteopathy.

Non limiting examples of disease according to the invention include, but are not limited to:

Neurodegenerative diseases such as tauopathies (such as Alzheimer's disease among others), synucleinopathies (such as Parkinson disease among others), Huntington disease and related polyglutamine diseases, polyalanine diseases (such as oculo-pharyngeal muscular dystrophy), prion diseases (also named transmissible spongiform encephalopathies), demyelination disorders such as Charcot-Marie Tooth diseases (also named hereditary motor and sensory neuropathy), leukodystrophies, amyotrophic lateral sclerosis (also referred to as motor neurone disease and as Lou Gehrig's disease), seipinopathies and multiple sclerosis.

Examples of tauopathies include, but are not limited to Alzheimer's disease, progressive supranuclear palsy, corticobasal degeneration, frontotemporal lobar degeneration or frontotemporal dementia (FTD) (Pick's disease). FTD is a neurodegenerative disease characterized by progressive neuronal loss predominantly involving the frontal and/or temporal lobes; second only to Alzheimer's disease (AD) in prevalence, FTD accounts for 20% of young onset dementia cases. The involvement of UPR in tauopathies is well documented (see Stoveken 2013, The Journal of Neuroscience 33(36):14285-14287). Without to be bound by a theory, it is anticipated that compounds of the invention which are PPP1R15A inhibitors will ameliorate disease manifestations of tauopathies. According to a preferred embodiment, the invention relates to a PPP1R15A inhibitor of formula (I) or a pharmaceutical acceptable salt thereof for the use in treating Alzheimer disease. According to a another preferred embodiment, the invention relates to a PPP1R15A inhibitor of formula (I) or a pharmaceutical acceptable salt thereof for the use in treating a disease selected among frontotemporal dementia (FTD), supranuclear palsy and corticobasal degeneration, preferably FTD.

Examples of synucleinopathies include, but are not limited to Parkinson's disease, dementia with Lewy bodies, pure autonomic failure, and multiple system atrophy. Recently, Colla et al. (J. of Neuroscience 2012 Vol. 32 N°10 pp 3306-3320) demonstrated that Salubrinal a small molecule that increases the phosphorylation of eIF2 alpha by inhibiting the PPP1R15A mediated dephosphorylation of eIF2α (Boyce et al. 2005 Science Vol. 307 pp 935-939), significantly attenuates disease manifestations in two animal models of alpha-synucleinopathy. Without to be bound by a theory, it is anticipated that compounds of the invention which are PPP1R15A inhibitors will ameliorate disease manifestations of alpha-syncleinopathies. According to a preferred embodiment, the invention relates to a PPP1R15A inhibitor of formula (I) or a pharmaceutical acceptable salt thereof for the use in treating alpha-syncleinopathies. According to a preferred embodiment, the invention relates to a PPP1R15A inhibitor of formula (I) or a pharmaceutical acceptable salt thereof for the use in treating Parkinson's disease.

Examples of polyglutamine diseases include but are not limited to Spinobulbar muscular atrophy (or Kennedy disease), Huntington disease, Dentatorubral-pallidoluysian atrophy, Spinocerebellar ataxia type 1, Spinocerebellar ataxia type 2, Spinocerebellar ataxia type 3 (or Machado-Joseph disease), Spinocerebellar ataxia type 6, Spinocerebellar ataxia type 7 and Spinocerebellar ataxia type 17. Guanabenz is able to attenuate the accumulation of mutant Huntingtin in cell-based assays (WO2008/041133). This finding is unexpected since mutant huntingtin is either cytosolic or nuclear. However, there is evidence that mutant huntingtin metabolism has previously been connected to the ER stress response (Nishitoh et al., 2002, Genes Dev, 16, 1345-55; Rousseau et al., 2004, Proc Natl Acad Sci USA, 101, 9648-53; Duennwald and Lindquist, 2008, Genes Dev, 22, 3308-19). The findings that guanabenz protects cells from cytotoxic ER stress and reduces mutant huntingtin accumulation further supports the idea that there may be aspects of the ER stress response that impact on mutant huntingtin accumulation. However, Guanabenz is not useful for the treatment of human protein misfolding diseases due to its hypotensive activity. In contrast, the Guanabenz derivative PPP1R15A inhibitors devoid of alpha2 adrenergic activity of the invention could be useful to treat polyglutamine diseases and more specifically selected in the group of Huntington disease, Spinobulbar muscular atrophy (or Kennedy disease), Dentatorubral-pallidoluysian atrophy, Spinocerebellar ataxia type 1, Spinocerebellar ataxia type 2, Spinocerebellar ataxia type 3 (or Machado-Joseph disease), Spinocerebellar ataxia type 6, Spinocerebellar ataxia type 7 and Spinocerebellar ataxia type 17. According to a preferred embodiment, the invention relates to a PPP1R15A inhibitor of formula (I) or a pharmaceutical acceptable salt thereof for the use in treating polyglutamine disease. According to a preferred embodiment, the invention relates to a PPP1R15A inhibitor of formula (I) or a pharmaceutical acceptable salt thereof for the use in treating Huntington disease.

Example of polyalanine diseases include oculo-pharyngeal muscular dystrophy which is caused by poly-alanine tract in poly(A) binding protein nuclear 1 (PABPN1). Barbezier et al. (2011, EMBO Vol. 3 pp 35-49) demonstrated that Guanabenz reduces aggregation in oculopharyngeal muscular atrophy. According to a preferred embodiment, the invention relates to a PPP1R15A inhibitor of formula (I) or a pharmaceutical acceptable salt thereof for the use in treating polyalanine disease. According to a preferred embodiment, the invention relates to a PPP1R15A inhibitor of formula (I) or a pharmaceutical acceptable salt thereof for the use in treating oculopharyngeal muscular atrophy.

Examples of prion diseases of humans include but are not limited to classic Creutzfeldt-Jakob disease, new variant Creutzfeldt-Jakob disease (nvCJD, a human disorder related to Bovine spongiform encephalopathy), Gerstmann-Sträussler-Scheinker syndrome, fatal familial insomnia and kuru. Guanabenz reduces the symptoms of prion infected mice (D. Tribouillard-Tanvier et al., 2008 PLoS One 3, e1981). However, Guanabenz is not useful for the treatment of human protein misfolding diseases due to its hypotensive activity. In contrast, the Guanabenz derivative PPP1R15A inhibitors devoid of alpha2 adrenergic activity of the invention could be useful to treat prion diseases. According to a preferred embodiment, the invention relates to a PPP1R15A inhibitor of formula (I) or a pharmaceutical acceptable salt thereof for the use in treating a disease selected in the group of Creutzfeldt-Jakob disease, new variant Creutzfeldt-Jakob disease, Gerstmann-Sträussler-Scheinker syndrome, fatal familial insomnia and kuru.

Demyelination disorders are characterized by a loss of oligodendrocytes in the central nervous system or Schwann cells in the peripheral nervous system. The phenomenon associated with a demyelination disorder is characterized by a decrease in myelinated axons in the central nervous system or peripheral nervous system. Non-limiting examples of misfolded proteins of a myelinating cell (including oligodendrocyte and Schwann cell) is selected from the group consisting of CC1, myelin basic protein (MBP), ceramide galactosyltransferase (CGT), myelin associated glycoprotein (MAG), myelin oligodendrocyte glycoprotein (MOG), oligodendrocyte-myelin glycoprotein (OMG), cyclic nucleotide phosphodiesterase (CNP), myelin protein zero (MPZ), peripheral myelin protein 22 (PMP22), Connexin 32 (Cx32), protein 2 (P2), galactocerebroside (GalC), sulfatide and proteolipid protein (PLP). MPZ, PMP22, Cx32 and P2 are preferred misfolded proteins for Schwann cells. PLP, MBP, MAG are preferred misfolded proteins for oligodendrocytes.

In certain embodiments, the demyelination disorder is selected from the group consisting of Charcot-Marie Tooth (CMT) diseases. CMT refer to a group of hereditary neuropathy disorders characterized by a chronic motor and sensory polyneuropathy. Different types of CMT were identified such as CMT1, CMT2, CMT4, CMTX and Dejerine-Sottas disease. CMT subtypes may be further subdivided primarily on molecular genetic findings. For examples CMT1 is subdivided in CMT1A, 1B, 1C, 1D, 1E, 1F/2E. Over a 100 mutations in the gene encoding myelin protein zero (P0), a single-pass transmembrane protein, which is the major protein produced by myelinating Schwann cells causes Charcot-Marie-Tooth neuropathy (D'Antonio et al., 2009, J Neurosci Res, 87, 3241-9). The mutations are dominantly inherited and cause the disease through a gain of toxic function (D'Antonio et al., 2009, J Neurosci Res, 87, 3241-9). Deletion of serine 63 from P0 (P0S63del) causes Charcot-Marie-Tooth 1B neuropathy in humans and a similar demyelinating neuropathy in transgenic mice. The mutant protein accumulates in the ER and induces the UPR (D'Antonio et al., 2009, J Neurosci Res, 87, 3241-9). Genetic ablation of CHOP, a pro-apoptotic gene in the UPR restores motor function in Charcot-Marie-Tooth mice (Pennuto et al., 2008, Neuron, 57, 393-405). The finding that PPP1R15A inhibition in cells nearly abolishes CHOP expression in ER-stressed cells indicates that genetic or pharmacological inhibition of PPP1R15A should reduce motor dysfunction in Charcot-Marie-Tooth mice. Recently, D'Antonio et al. (2013 J. Exp. Med Vol. pp 1-18) demonstrated that P0S63del mice treated with salubrinal, regained almost normal motor capacity in rotarod analysis and was accompanied by a rescue of morphological and electrophysiological abnormalities. Accumulation of the of CMT-related mutant in the ER proteins is not unique to P0S63del; at least five other P0 mutants have been identified that are retained in the ER and elicit an UPR (Pennuto et al., 2008 Neuron Vol. 57 pp 393-405; Saporta et al., 2012 Brain Vol. 135 pp 2032-2047). In addition, protein misfolding and accumulation of misfolded protein in the ER have been implicated in the pathogenesis of other CMT neuropathies as a result of mutations in PMP22 and Cx32 (Colby et al., 2000 Neurobiol. Disease Vol. 7 pp 561-573; Kleopa et al., 2002 J. Neurosci. Res. Vol. 68 pp 522-534; Yum et al., 2002 Neurobiol. Dis. Vol. 11 pp 43-52). However, Salubrinal is toxic and cannot be used to treat human patients D'Antonio et al. (2013 J. Exp. Med Vol. pp 1-18). In contrast, the PPP1R15A inhibitors of formula (I) are predicted to be safe and could be useful for the treatment of CMTs, preferably CMT-1A and 1B. According to a preferred embodiment, the invention relates to a PPP1R15A inhibitor of formula (I) or a pharmaceutical acceptable salt thereof for the use in treating CMT, more preferably CMT-1 and Dejerine-Sottas disease. According to a preferred embodiment, the invention relates to a PPP1R15A inhibitor of formula (I) or a pharmaceutical acceptable salt thereof for the use in treating CMT associated with an accumulation of misfolded protein in the ER. According to a preferred embodiment, the invention relates to a PPP1R15A inhibitor of formula (I) or a pharmaceutical acceptable salt thereof for the use in treating CMT-1A. According to a preferred embodiment, the invention relates to a PPP1R15A inhibitor of formula (I) or a pharmaceutical acceptable salt thereof for the use in treating CMT-1B. According to a preferred embodiment, the invention relates to a PPP1R15A inhibitor of formula (I) or a pharmaceutical acceptable salt thereof for the use in treating CMT-1E.

In another embodiment, the compound of formula (I) is for use in treating CMT, more preferably for use in treating CMT-1, in association with at least one compound selected in the group of D-Sorbitol, baclofen, pilocarpine, naltrexone, methimazole, mifepristone, ketoprofene and salts thereof. According to another embodiment, the invention relates to guanabenz or salubrinal (i.e. PPP1R15A inhibitors) or a pharmaceutical acceptable salt thereof for the use in treating CMT, preferably CMT-1, in association with at least one compound selected in the group of D-Sorbitol, baclofen, pilocarpine, naltrexone, methimazole, mifepristone, ketoprofene and salts thereof. The compounds are combined for a grouped or separate administration, simultaneously or sequentially.

The invention relates to composition comprising a PPP1R15A inhibitor selected in the group of compound of formula (I), guanabenz and salubrinal or a pharmaceutical acceptable salt thereof, and at least one marketed compound and salts thereof, for use in the treatment of neurodegenerative diseases, preferably CMT, more preferably CMT-1. The dosage of compounds in the composition shall lie within the range of doses not above the usually prescribed doses for long term maintenance treatment or proven to be safe on phase 3 clinical trial; the most preferred dosage of compounds in the combination shall corresponds to amounts for 1% up to 10% of those usually prescribes for long term maintenance treatment.

Thus, the invention relates to composition comprising a PPP1R15A inhibitor selected in the group of compound of formula (I), guanabenz and salubrinal or a pharmaceutical acceptable salt thereof, and a compound increasing the expression of PMP22 protein, selected in the group of D-Sorbitol, baclofen, pilocarpine, naltrexone, methimazole, mifepristone, ketoprofene and salts thereof, for use in the treatment of CMT, preferably CMT-1, more preferably CMT-1A.

In other embodiments, the demyelination disorder is selected from the group consisting of leukodystrophies. Examples of leukodystrophies include but are not limited to adrenoleukodystrophy (ALD), Alexander disease, Canavan disease, Krabbe disease, Metachromatic Leukodystrophy (MLD), Pelizaeus-Merzbacher disease (PMD), childhood ataxia with central nervous system hypomyelination (also known as vanishing white matter disease), CAMFAK syndrome, Refsum Disease, Cockayne Syndrome, Ver der Knapp Syndrome, Zellweger Syndrome, Guillain-Barre Syndrome (GBS), chronic inflammatory demyelinating polyneuropathy (CIDP), multifocal motor neuropathy (MMN) and progressive supernuclear palsy, progressive Multifocal Leuko-encephalopathy (PML), Encephalomyelitis, Central Pontine Myelolysis (CPM), Anti-MAG Disease, among others. Gow et al. (Neuron, 2002 Vol. 36, 585-596) demonstrated that the unfolded protein response is activated in PMD, and show that this pathway is duplication of, the PLP1 gene.

According to a preferred embodiment, the invention relates to a PPP1R15A inhibitor of formula (I) or a pharmaceutical acceptable salt thereof for the use in treating leukodystrophies, and preferably Pelizaeus-Merzbacher disease (PMD).

Amyotrophic lateral sclerosis (ALS) is referred to as motor neurone disease and as Lou Gehrig's disease. It is now well recognized that protein misfolding plays a central role in both familial and sporadic ALS (Matus et al. 2013 Int. J. Cell Biol. ID674751 http://dx.doi.org/10.1155/2013/674751). Saxena et al. (Nature Neuroscience 2009 Vol. 12 pp 627-636) demonstrated that Salubrinal extends the life span of a G93A-SOD1 transgenic mouse model of motor neuron disease. More recently, Jiang et al. (Neuroscience 2014) demonstrated that Guanabenz delays the onset of disease symptoms, extends lifespan, improves motor performance and attenuates motor neuron loss in the SOD1 G93A mouse model of ALS. Das et al. (2015 Science 388, 239-242) demonstrated that a guanabenz derivative prevents the motor, morphological and molecular defects of ALS in mutant G93A SOD1 mice. According to a preferred embodiment, the invention relates to a PPP1R15A inhibitor of formula (I) or a pharmaceutical acceptable salt thereof for the use in treating familial and sporadic forms of ALS.

Examples of seipinopathies include, but are not limited to Berardinelli-Seip congenital lipodystrophy type 2 (BSCL2)-related motor disease, congenital generalized lipodystrophy (CGL), Silver syndrome, distal hereditary motor neuropathy type V (dHMN-V). The expression of mutant forms of seipin in cultured cells activates the unfolded protein response (UPR) pathway and induces ER stress-mediated cell death (Ito & Suzuki, 2009 Brain 132: 87-15). According to a preferred embodiment, the invention relates to a PPP1R15A inhibitor of formula (I) or a pharmaceutical acceptable salt thereof for the use in treating seipinopathy.

In another embodiment, the demyelination disorder referred therein is multiple sclerosis and related disease such as Schilder's disease. According to a preferred embodiment, the invention relates to a PPP1R15A inhibitor of formula (I) or a pharmaceutical acceptable salt thereof for the use in treating multiple sclerosis.

Cystic Fibrosis (CF)

Norez et al. (2008 Eur. J. Pharmacol. Vol. 592 pp 33-40) demonstrated that Guanabenz activates $Ca^{2+}$ dependent chloride currents in cystic fibrosis human airway epithelial cells. Without to be bound by a theory, it is anticipated that compounds of the invention which are guanabenz derivative PPP1R15A inhibitors will ameliorate disease manifestations of cystic fibrosis. According to a preferred embodiment, the invention relates to a PPP1R15A inhibitor of formula (I) or a pharmaceutical acceptable salt thereof for the use in treating cystic fibrosis.

Retinal Diseases.

Recently published literature has provided evidences that the UPR is involved in the development of retinal degeneration: inherited retinal degeneration such as retinal ciliopathies & retinitis pigmentosa, macular degeneration, retinopathy of premarurity, light-induced retinal degeneration, retinal detachment, diabetic retinopathy and glaucoma (for review Gorbatyuk et Gorbatyuk 2013 Molecular Vision Vol. 19 pp 1985-1998; Jing et al., 2012, Exp Diabetes Res, 2012, 589589).

Retinal ciliopathies are a group of rare genetic disorders originating from a defect in the primary cilium of photoreceptors thus inducing retinitis pigmentosa. This defect has been reported to induce an ER stress due to protein accumulation in the inner segment of the photoreceptor which in turn induces the UPR (WO2013/124484). Retinal degeneration is a very common feature in ciliopathies that can be observed either in isolated retinitis pigmentosa such as Leber's congenital amaurosis or X-linked retinitis pigmentosa, or also in syndromic conditions like the Bardet-Biedl Syndrome (BBS), the Alström syndrome (ALMS) or the Usher syndrome. The retinal ciliopathy is selected from the group consisting of Bardet-Biedl syndrome, Senior-Loken syndrome, Joubert syndrome, Salidono-Mainzer syndrome, Sensenbrenner syndrome, Jeune syndrome, Meckel-Gruder syndrome, Alström syndrome, MORM syndrome. In one preferred embodiment, the compound of formula (I) is for use in treating retinal diseases, more preferably, inherited retinal degeneration such as retinal ciliopathies & retinitis pigmentosa, macular degeneration, retinopathy of premarurity, light-induced retinal degeneration, retinal detachment, diabetic retinopathy and glaucoma.

According to a preferred embodiment, the invention relates to a PPP1R15A inhibitor of formula (I) or a pharmaceutical acceptable salt thereof for the use in treating retinitis pigmentosa. According to a preferred embodiment, the invention relates to a PPP1R15A inhibitor of formula (I)

or a pharmaceutical acceptable salt thereof for the use in treating Leber's congenital amaurosis. According to another preferred embodiment, the invention relates to a PPP1R15A inhibitor of formula (I) or a pharmaceutical acceptable salt thereof for the use in treating Bardet-Biedl syndrome. According to another preferred embodiment, the invention relates to a PPP1R15A inhibitor of formula (I) or a pharmaceutical acceptable salt thereof for the use in treating Alström syndrome. According to another preferred embodiment, the invention relates to a PPP1R15A inhibitor of formula (I) or a pharmaceutical acceptable salt thereof for the use in treating Husher syndrome.

In preferred embodiment, the compound of formula (I) is for use in treating retinal diseases, more preferably for use in treating diseases selected in the group of inherited retinal degeneration such as retinal ciliopathies, retinitis pigmentosa, macular degeneration, retinopathy of premarurity, light-induced retinal degeneration, retinal detachment, diabetic retinopathy and glaucoma in association with a compound increasing the expression and/or the activity of BIP protein, such as Valproic acid or a derivative thereof, trichostatin A, lithium, 1-(3,4-dihydroxy-penyl)-2-thiocyanate-ethanone and exendin-4. Thus, the invention relates to composition comprising a PPP1R15A inhibitor of formula (I) or a pharmaceutical acceptable salt thereof and a compound increasing the expression and/or the activity of BIP protein, preferably Valproic acid, for use in the treatment of diseases selected in the group of inherited retinal degeneration such as retinal ciliopathies, retinitis pigmentosa, macular degeneration, retinopathy of premarurity, light-induced retinal degeneration, retinal detachment, diabetic retinopathy and glaucoma.

In preferred embodiment, the compound of formula (I), is for use in treating retinal diseases, more preferably for use in treating diseases selected in the group of inherited retinal degeneration such as retinal ciliopathies, retinitis pigmentosa, macular degeneration, retinopathy of premarurity, light-induced retinal degeneration, retinal detachment, diabetic retinopathy and glaucoma in association with a gene therapy vectors, Non limiting examples of gene therapy vectors include lentivirus, adenovirus, and adeno-associated vectors (AAVs); these vectors are effective in delivering genes of interest to the retina and retinal pigment epithelium for ocular gene therapy. It is anticipated that in an ocular gene therapy of inherited retinal degeneration associated with an accumulation of mutated misfolded proteins, protein accumulation in the endoplasmic reticulum will remain present while a normal protein is expressed from the gene therapy vector. It remains the need to decrease the protein accumulation/load in the cell, preferably in the ER with PPP1R15A inhibitors. The invention also relates to composition comprising PPP1R15A inhibitor selected in the group of compound of formula (I), guanabenz and salubrinal or a pharmaceutical acceptable salt thereof, in combination with ocular gene therapy.

Lysosomal Storage Diseases;

Lysosomal storage diseases are a group of approximately 50 rare inherited metabolic disorders that result from defects in lysosomal function. The lysosomal dysfunction is usually the consequence of deficiency of a single enzyme required for the metabolism of lipids, glycoproteins or so-called mucopolysaccharides. Examples of lysosomal storage diseases which can be treated with by PPP1R15A inhibitors of formula (I)) described herein include, but are not limited to, Activator Deficiency/GM2 gangliosidosis, alpha-mannosidosis, aspartylglucosaminuria, cholesteryl ester storage disease, cystinosis, Danon disease, Fabry disease, Farber disease, Niemann-Pick disease, fucosidosis, galactosialidosis, Gaucher disease (Types I, II, II), GM1 gangliosidosis (infantile, late infantile/juvenile, adult/chronic), I-cell disease/Mucolipidosis, Infantile free sialic acid storage disease/ISSD, Juvenile hexosaminidase A deficiency, Krabbe disease (infantile onset, late onset), lysosomal acid lipase deficiency (early onset/late onset), metachromatic leukodystrophy, mucopolysaccharidoses disorders (such as Pseudo-Hurler polydystrophy/mucolipidosis IIIA, mucopolysaccharidosis I (MPS I) Hurler syndrome, MPS I Scheie syndrome, MPS I Hurler-Scheie syndrome, MPS II Hunter syndrome, Sanfilippo syndrome Type A (MPS IIIA), Sanfilippo syndrome Type B (MPS IIIB), Sanfilippo syndrome Type C (MPS IIIC), Sanfilippo syndrome Type D (MPS IIID), Morquio Type A/MPS IVA, Morquio Type B/MPS IVB, MPS IX hyaluronidase deficiency, MPS VI Maroteaux-Lamy, MPS VII Sly syndrome, mucopolylipidosis I/sialidosis, mucolipidosis IIIC, mucolipidosis type IV (multiple sulfatase deficiency, Niemann-Pick disease (Types A, B, C), CLN6 disease (atypical late infantile, late onset variant, early juvenile), Batten-Spielmeyer-Vogt/Juvenile NCL/CLN3 disease, Finnish Variant late infantile CLNS, Jansky-Bielschosky disease/late infantile CLN2/TPP1 disease, Kufs/Adult-onset NCL/CLN4 disease, Northern epilepsy/variant late infantile CLN8, Santavuori-Haltia/infantile CLN1/PPT disease, beta-mannosidosis, Pompe disease/glycogen storage disease type II, pycnodysostosis, Sandhoff disease/GM2 gangliosidosis (adult onset, infantile onset, juvenile onset), Schindler disease, SalI disease/sialic acid storage disease, Tay-Sachs/GM2 gangliosidosis, and Wolman disease. According to another preferred embodiment, the invention relates to a PPP1R15A inhibitor of formula (I) or a pharmaceutical acceptable salt thereof for the use in treating lysosomal storage diseases which are the consequence of deficiency of at least one single enzyme required for the metabolism of lipids, glycoproteins or so-called muco-polysaccharides and wherein said enzyme is misfolded in the endoplasmic reticulum (ER). According to a preferred embodiment, the lysosomal storage disease is Gaucher disease.

Amyloidosis Diseases:

Amyloidosis is a non-specific term that refers to a number of different diseases collectively called amyloidosis. Amyloids are proteins whose secondary structure change, causing the proteins to fold in a characteristic form, the beta-pleated sheet. When the normally soluble proteins fold to become amyloids, they become insoluble, deposit and accumulate in organs or tissues, disrupting normal function. Different types of amyloidosis have different signs and symptoms depending on where and in which organs the amyloid proteins aggregate. Example of amyloidosis diseases includes, but are not limited to, AL, AH, ALH amyloidosis (amyloid derived from light-chain, heavy-chain, heavy and light chain antibodies respectively), AA amyloidosis (amyloid derived from derived from serum A protein), ATTR amyloidosis (amyloid derived from transthyrethin), primary systemic amyloidosis, secondary systemic amyloidosis, senile systemic amyloidosis, familial amyloid polyneuropathy 1, hereditary cerebral amyloid angiopathy, hemodialysis-related amyloidosis, familial amyloid polyneuropathy III, Finnish hereditary systemic amyloidosis, atrial amyloidosis, hereditary non-neuropathic systemic amyloidosis, injection-localized amyloidosis, hereditary renal amyloidosis and Alzheimer disease among others. According to another preferred embodiment, the amyloid is Amyloid beta (Aβ or Abeta) and the invention relates to a PPP1R15A inhibitor of formula (I) or (II) or a pharmaceutical acceptable salt thereof for the use in treating Alzheimer disease.

According to another preferred embodiment, the amyloid is HLA-B27 (Colbert et al. 2009 Prion Vol. 3 (1) pp 15-16) and the invention relates to a PPP1R15A inhibitor of formula (I) or a pharmaceutical acceptable salt thereof for the use in treating spondylo-arthropathies, more preferably ankylosing spondylitis.

Inflammation

PPP1R15A represents a promising target to control inflammation by blocking the release of inflammatory cytokines and other secreted molecular mediators leading to pathogenic conditions. Non-limiting examples of diseases or conditions having inflammation associated therewith which can be treated with by PPP1R15A inhibitors of formula (I) described herein include, but are not limited to infection-related or non-infectious inflammatory conditions in the lung (i.e., sepsis, lung infections, Respiratory Distress Syndrome, bronchopulmonary dysplasia, etc.); infection-related or non-infectious inflammatory conditions in other organs such as colitis, ulcerative colitis, Inflammatory Bowel Disease, diabetic nephropathy, hemorrhagic shock, spondyloarthropathies, pancreatitis; inflammation-induced cancer (i.e., cancer progression in patients with colitis or Inflammatory Bowel Disease); and the like.

Examples of such pathogenic inflammatory conditions include auto-immune diseases, hereditary diseases, chronic diseases and infectious diseases such as allergy, asthma, hypercytokinemia including graft versus host disease (GVHD), acute respiratory distress syndrome (ARDS), sepsis, systemic inflammatory response syndrome (SIRS) (see WO2011/061340). Preferably, infectious disease is selected from influenza virus infection, smallpox virus infection, herpes virus infection, severe acute respiratory syndrome (SARS), chikungunya virus infection, West Nile Virus infection, dengue virus infection, Japanese encephalitis virus infection, yellow fever virus infection, and hepatitis C virus infection.

Preferably auto-immune disease is selected from Sjögren's syndrome, systemic lupus erythematosus, psoriasis, dermatitis herpetiformis, vitiligo, mycosis fungoides, allergic contact dermatitis, atopic dermatitis, lichen planus, Pityriasis lichenoides et varioliforms acuta (PLEVA), arthritis, catastrophic antiphospholipid syndrome.

According to another preferred embodiment, the invention relates to a PPP1R15A inhibitor of formula (I) or a pharmaceutical acceptable salt thereof for the use in treating a disease selected in the group of colitis, ulcerative colitis, Inflammatory Bowel Disease, pancreatitis, sepsis. According to another preferred embodiment, the invention relates to a PPP1R15A inhibitor of formula (I) or a pharmaceutical acceptable salt thereof, for the use in treating pancreatitis. According to another preferred embodiment, the invention relates to a PPP1R15A inhibitor of formula (I) or a pharmaceutical acceptable salt thereof, for the use in treating sepsis.

According to another preferred embodiment, the invention relates to a PPP1R15A inhibitor of formula (I) or a pharmaceutical acceptable salt thereof for the use in treating spondylo-arthropathies, more preferably ankylosing spondylitis.

Metabolic and/or cardio-vascular disorders, such adiposity, hyper-lipidemia, familial hyper-cholesterolemia, obesity, atherosclerosis, hypertension, heart diseases, cardiac ischaemia, stroke, myocardial infraction, trans-aortic constriction, vascular stroke and diabetes and related disorders include hyperglycemia, impaired glucose tolerance, hyper-insulinemia (pre-diabetes), insulin hypersensitivity type I and II diabetes, insulin resistance, Wolcott-Rallison Syndrome among others.

In one preferred embodiment, the compound of formula (I) is for use in treating atherosclerosis. In second preferred embodiment, the compound of formula (I) is for use in treating a disease selected in the group of hypertension, heart diseases, cardiac ischaemia, stroke, myocardial infraction, trans-aortic constriction or vascular stroke. In one preferred embodiment, the compound of formula (I) is for use in treating cardiac ischemia. In another preferred embodiment, the compound of formula (I) is for use in treating a disease selected in the group of hyperglycemia, impaired glucose tolerance, hyper-insulinemia (pre-diabetes), insulin hypersensitivity type I and II, insulin resistance and Wolcott-Rallison Syndrome. In another preferred embodiment, the compound of formula (I) is for use in treating pre-diabetes or diabetes, more preferably type 2 diabetes.

Osteoporosis:

Yokota et al. (BMC Musculoskeletal disorders 2013, 14, 197) and He et al. (Cellular Signaling 2013, 25 552-560) demonstrated that Salubrinal (Boyce et al. 2005) efficiently block osteoporosis in mice model and stimulates bone formation. However, Salubrinal is toxic and cannot be used to treat human patients. In contrast, the PPP1R15A inhibitors of formula (I) are predicted to be safe and could be useful for the treatment of osteoporosis. In one preferred embodiment, the compound of formula (I) is for use in treating osteoporosis.

Nervous System Trauma

Ohri et al. (Neurobiology of disease, 2013 Vol. 58 pp 29-37) demonstrated that Salubrinal significantly improved hindlimb locomotion which corresponds with an improved white matter sparing and a decreased oligodendrocytes apoptosis, thus improving functional recovery after spinal cord injury.

The PPP1R15A inhibitors of formula (I) of the invention are predicted to be safe and could be useful to reduce the oligodendrocyte loss after traumatic spinal cord injury and for the prophylactic and/or therapeutic treatment of spinal cord injury. In one preferred embodiment, the compound of formula (I) is for the prophylactic and/or therapeutic treatment of spinal cord injury.

Ischemia, Cerebral Ischemia, Sleep Apnoea

The present invention provides methods of using PPP1R15A inhibitors of formula (I) of the invention to prevent and/or treat tissue damage resulting from cell damage or death due to necrosis or apoptosis. Example of neural tissue damage include ischemia and reperfusion injury, such as cerebral ischemic stroke and head trauma. In one preferred embodiment, the compound of formula (I) is for the prophylactic and/or therapeutic treatment of cerebral ischemia, such as cerebral ischemic stroke and head trauma.

Aging

Aging is associated with the degeneration of cells, tissues, and organs, resulting in diseases such as cancer, cardiovascular failure, obesity, type 2 diabetes mellitus, non-alcoholic fatty liver, and neurodegenerative diseases, as well as the decline of most measures of physiological performance.

In biology, senescence is the state or process of aging. Cellular senescence is a phenomenon where isolated cells demonstrate a limited ability to divide in culture (the Hayflick Limit, discovered by Leonard Hayflick in 1961), while organismal senescence is the ageing of organisms. Organismal senescence is characterised by the declining ability to respond to stress, increasing homeostatic imbalance and the increased risk of disease; in particular, the UPR is impaired with age (Naidoo et al., 2008, J Neurosci, 28, 6539-48). Thus, prolonging the beneficial effect of the UPR by inhibition of eIF2α phosphatase could ameliorate age-related disorders. Therefore, the PPP1R15A inhibitors of formula (I) of the invention are predicted to be safe and could be useful to prevent and/or treat diseases or disorders relating to lifespan or proliferative capacity of cells, and diseases or disease conditions induced or exacerbated by cellular senescence in an animal, more specifically humans.

According to a particular embodiment, the present invention concerns one compound selected from:

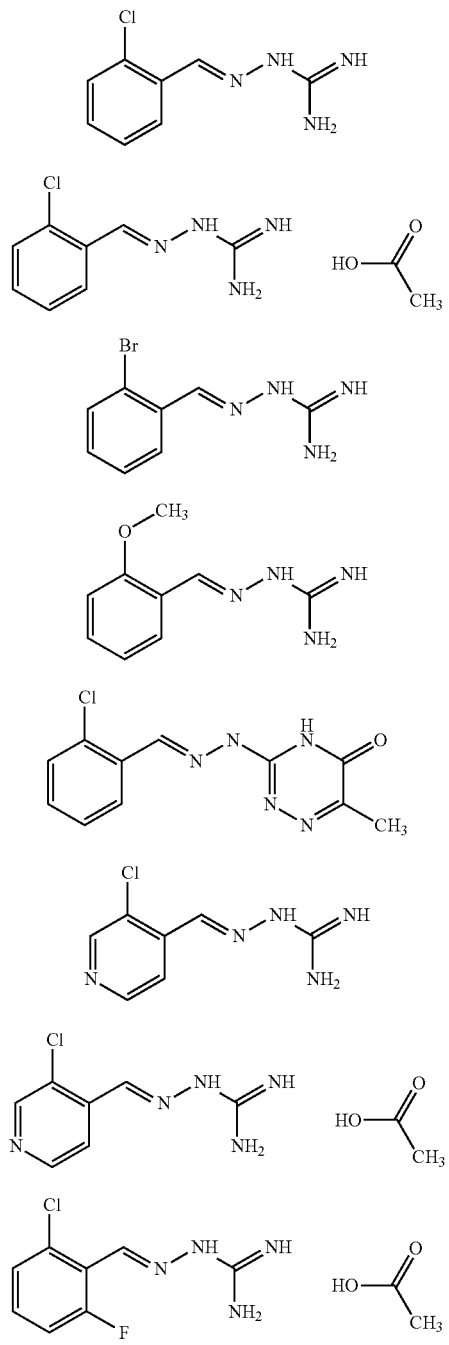

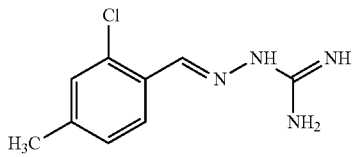

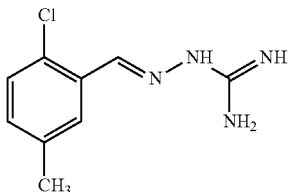

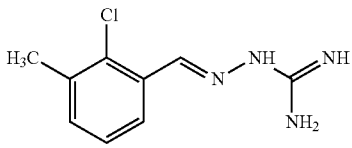

For use in the treatment and/or prevention of one or more diseases selected from selected in the group of cystic fibrosis, lysosomal storage disease, amyloidosis diseases, cancers, inflammation preferably sepsis, colitis and pancreatitis, metabolic disorders, diabetes, cardio-vascular disorders, osteoporosis, central nervous system trauma, ischemia, retinal diseases, seipinopathies, neurodegenerative diseases, preferably Alzheimer's disease, Parkinson's disease, Amyotrophic Lateral Sclerosis, Huntington's disease, polyglutamine and polyalanine diseases, Charcot-Marie-Tooth diseases, leukodystrophies and multiple sclerosis.

According to an embodiment, the present invention also concerns one compound selected from the above compounds 1 to 11, as well as the pharmaceutical compositions comprising the same.

Pharmaceutical Compositions

For use according to the present invention, the compounds or physiologically acceptable salts, esters or other physiologically functional derivatives thereof, described herein, may be presented as a pharmaceutical formulation, comprising the compounds or physiologically acceptable salt, ester or other physiologically functional derivative thereof, together with one or more pharmaceutically acceptable carriers therefore and optionally other therapeutic and/or prophylactic ingredients. The carrier(s) must be acceptable in the sense of being compatible with the other ingredients of the formulation and not deleterious to the recipient thereof. The pharmaceutical compositions may be for human or animal usage in human and veterinary medicine.

Examples of such suitable excipients for the various different forms of pharmaceutical compositions described herein may be found in the "Handbook of Pharmaceutical Excipients, $2^{nd}$ Edition, (1994), Edited by A Wade and P J Weller.

Acceptable carriers or diluents for therapeutic use are well known in the pharmaceutical art, and are described, for example, in Remington's Pharmaceutical Sciences, Mack Publishing Co. (A. R. Gennaro edit. 1985).

Examples of suitable carriers include lactose, starch, glucose, methyl cellulose, magnesium stearate, mannitol, sorbitol and the like. Examples of suitable diluents include ethanol, glycerol and water.

The choice of pharmaceutical carrier, excipient or diluent can be selected with regard to the intended route of administration and standard pharmaceutical practice. The pharmaceutical compositions may comprise as, or in addition to, the carrier, excipient or diluent any suitable binder(s), lubricant(s), suspending agent(s), coating agent(s), solubilising agent(s), buffer(s), flavouring agent(s), surface active agent(s), thickener(s), preservative(s) (including anti-oxidants) and the like, and substances included for the purpose of rendering the formulation isotonic with the blood of the intended recipient.

Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol.

Examples of suitable lubricants include sodium oleate, sodium stearate, magnesium stearate, sodium benzoate, sodium acetate, sodium chloride and the like.

Preservatives, stabilizers, dyes and even flavoring agents may be provided in the pharmaceutical composition. Examples of preservatives include sodium benzoate, sorbic acid and esters of p-hydroxybenzoic acid. Antioxidants and suspending agents may be also used.

Pharmaceutical formulations include those suitable for oral, topical (including dermal, buccal, ocular and sublingual), rectal or parenteral (including subcutaneous, intradermal, intramuscular and intravenous), nasal, intra-ocularly and pulmonary administration e.g., by inhalation. The formulation may, where appropriate, be conveniently presented in discrete dosage units and may be prepared by any of the methods well known in the art of pharmacy. All methods include the step of bringing into association an active compound with liquid carriers or finely divided solid carriers or both and then, if necessary, shaping the product into the desired formulation.

Pharmaceutical formulations suitable for oral administration wherein the carrier is a solid are most preferably presented as unit dose formulations such as boluses, capsules or tablets each containing a predetermined amount of active compound. A tablet may be made by compression or moulding, optionally with one or more accessory ingredients. Compressed tablets may be prepared by compressing in a suitable machine an active compound in a free-flowing form such as a powder or granules optionally mixed with a binder, lubricant, inert diluent, lubricating agent, surface-active agent or dispersing agent. Moulded tablets may be made by moulding an active compound with an inert liquid diluent. Tablets may be optionally coated and, if uncoated, may optionally be scored. Capsules may be prepared by filling an active compound, either alone or in admixture with one or more accessory ingredients, into the capsule shells and then sealing them in the usual manner. Cachets are analogous to capsules wherein an active compound together with any accessory ingredient(s) is sealed in a rice paper envelope. An active compound may also be formulated as dispersible granules, which may for example be suspended in water before administration, or sprinkled on food. The granules may be packaged, e.g., in a sachet.

Formulations suitable for oral administration wherein the carrier is a liquid may be presented as a solution or a suspension in an aqueous or non-aqueous liquid, or as an oil-in-water liquid emulsion.

Formulations for oral administration include controlled release dosage forms, e.g., tablets wherein an active compound is formulated in an appropriate release-controlling matrix, or is coated with a suitable release-controlling film. Such formulations may be particularly convenient for prophylactic use.

Pharmaceutical formulations suitable for rectal administration wherein the carrier is a solid are most preferably presented as unit dose suppositories. Suitable carriers include cocoa butter and other materials commonly used in the art. The suppositories may be conveniently formed by admixture of an active compound with the softened or melted carrier(s) followed by chilling and shaping in moulds.

Pharmaceutical formulations suitable for parenteral administration include sterile solutions or suspensions of an active compound in aqueous or oleaginous vehicles.

Pharmaceutical formulations of the invention are suitable for ophthalmic administration, in particular for intra-ocular, intra-vitreal, topical ocular or peri-ocular administration, more preferably for topical ocular or intra-vitreal administration.

Injectable preparations may be adapted for bolus injection or continuous infusion. Such preparations are conveniently presented in unit dose or multi-dose containers which are sealed after introduction of the formulation until required for use. Alternatively, an active compound may be in powder form which is constituted with a suitable vehicle, such as sterile, pyrogen-free water, before use.

An active compound may also be formulated as long-acting depot preparations, which may be administered by intramuscular injection or by implantation, e.g., subcutaneously or intramuscularly. Depot preparations may include, for example, suitable polymeric or hydrophobic materials, or ion-exchange resins. Such long-acting formulations are particularly convenient for prophylactic use.

Formulations suitable for pulmonary administration via the buccal cavity are presented such that particles containing an active compound and desirably having a diameter in the range of 0.5 to 7 microns are delivered in the bronchial tree of the recipient. As one possibility such formulations are in the form of finely comminuted powders which may conveniently be presented either in a pierceable capsule, suitably of, for example, gelatin, for use in an inhalation device, or alternatively as a self-propelling formulation comprising an active compound, a suitable liquid or gaseous propellant and optionally other ingredients such as a surfactant and/or a solid diluent. Suitable liquid propellants include propane and the chlorofluorocarbons, and suitable gaseous propellants include carbon dioxide. Self-propelling formulations may also be employed wherein an active compound is dispensed in the form of droplets of solution or suspension.

Such self-propelling formulations are analogous to those known in the art and may be prepared by established procedures. Suitably they are presented in a container provided with either a manually-operable or automatically functioning valve having the desired spray characteristics; advantageously the valve is of a metered type delivering a fixed volume, for example, 25 to 100 microlitres, upon each operation thereof.

As a further possibility an active compound may be in the form of a solution or suspension for use in an atomizer or nebuliser whereby an accelerated airstream or ultrasonic agitation is employed to produce a fine droplet mist for inhalation.

Formulations suitable for nasal administration include preparations generally similar to those described above for pulmonary administration. When dispensed such formulations should desirably have a particle diameter in the range 10 to 200 microns to enable retention in the nasal cavity; this may be achieved by, as appropriate, use of a powder of a suitable particle size or choice of an appropriate valve. Other suitable formulations include coarse powders having a particle diameter in the range 20 to 500 microns, for administration by rapid inhalation through the nasal passage from a container held close up to the nose, and nasal drops comprising 0.2 to 5% w/v of an active compound in aqueous or oily solution or suspension.

Pharmaceutically acceptable carriers are well known to those skilled in the art and include, but are not limited to, 0.1 M and preferably 0.05 M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Preservatives and other additives may also be present, such as, for example, antimicrobials, anti-oxydants, chelating agents, inert gases and the like.

Formulations suitable for topical formulation may be provided for example as gels, creams or ointments. Such preparations may be applied e.g. to a wound or ulcer either directly spread upon the surface of the wound or ulcer or carried on a suitable support such as a bandage, gauze, mesh or the like which may be applied to and over the area to be treated.

Liquid or powder formulations may also be provided which can be sprayed or sprinkled directly onto the site to be treated, e.g. a wound or ulcer. Alternatively, a carrier such as a bandage, gauze, mesh or the like can be sprayed or sprinkle with the formulation and then applied to the site to be treated.

According to a further aspect of the invention, there is provided a process for the preparation of a pharmaceutical or veterinary composition as described above, the process comprising bringing the active compound(s) into association with the carrier, for example by admixture.

In general, the formulations are prepared by uniformly and intimately bringing into association the active agent with liquid carriers or finely divided solid carriers or both, and then if necessary shaping the product. The invention extends to methods for preparing a pharmaceutical composition comprising bringing a compound of general formula (I) in conjunction or association with a pharmaceutically or veterinarily acceptable carrier or vehicle.

Salts/Esters

The compounds of the invention can be present as salts or esters, in particular pharmaceutically and veterinarily acceptable salts or esters.

Pharmaceutically acceptable salts of the compounds of the invention include suitable acid addition or base salts thereof. A review of suitable pharmaceutical salts may be found in Berge et al, J Pharm Sci, 66, 1-19 (1977). Salts are formed, for example with strong inorganic acids such as mineral acids, e.g. hydrohalic acids such as hydrochloride, hydrobromide and hydroiodide, sulfuric acid, phosphoric acid sulphate, bisulphate, hemisulphate, thiocyanate, persulphate and sulphonic acids; with strong organic carboxylic acids, such as alkanecarboxylic acids of 1 to 4 carbon atoms which are unsubstituted or substituted (e.g., by halogen), such as acetic acid; with saturated or unsaturated dicarboxylic acids, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as ($C_1$-$C_4$)-alkyl- or aryl-sulfonic acids which are unsubstituted or substituted (for example, by a halogen) such as methane- or p-toluene sulfonic acid. Salts which are not pharmaceutically or veterinarily acceptable may still be valuable as intermediates.

Preferred salts include, for example, acetate, trifluoroacetate, lactate, gluconate, citrate, tartrate, maleate, malate, pantothenate, adipate, alginate, aspartate, benzoate, butyrate, digluconate, cyclopentanate, glucoheptanate, glycerophosphate, oxalate, heptanoate, hexanoate, fumarate, nicotinate, palmoate, pectinate, 3-phenylpropionate, picrate, pivalate, proprionate, tartrate, lactobionate, pivolate, camphorate, undecanoate and succinate, organic sulphonic acids such as methanesulphonate, ethanesulphonate, 2-hydroxyethane sulphonate, camphorsulphonate, 2-naphthalenesulphonate, benzenesulphonate, p-chlorobenzenesulphonate and p-toluenesulphonate; and inorganic acids such as hydrochloride, hydrobromide, hydroiodide, sulphate, bisulphate, hemisulphate, thiocyanate, persulphate, phosphoric and sulphonic acids. According to a preferred embodiment the salt is acetate.

Esters are formed either using organic acids or alcohols/hydroxides, depending on the functional group being esterified. Organic acids include carboxylic acids, such as alkanecarboxylic acids of 1 to 12 carbon atoms which are unsubstituted or substituted (e.g., by halogen), such as acetic acid; with saturated or unsaturated dicarboxylic acid, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as ($C_1$-$C_4$)-alkyl- or aryl-sulfonic acids which are unsubstituted or substituted (for example, by a halogen) such as methane- or p-toluene sulfonic acid. Suitable hydroxides include inorganic hydroxides, such as sodium hydroxide, potassium hydroxide, calcium hydroxide, aluminium hydroxide. Alcohols include alkanealcohols of 1-12 carbon atoms which may be unsubstituted or substituted, e.g. by a halogen).

Enantiomers/Tautomers

In all aspects of the present invention previously discussed, the invention includes, where appropriate all enantiomers, diastereoisomers and tautomers of the compounds of the invention. The person skilled in the art will recognise compounds that possess optical properties (one or more chiral carbon atoms) or tautomeric characteristics. The corresponding enantiomers and/or tautomers may be isolated/prepared by methods known in the art. Enantiomers are characterised by the absolute configuration of their chiral centres and described by the R- and S-sequencing rules of Cahn, Ingold and Prelog. Such conventions are well known in the art (e.g. see 'Advanced Organic Chemistry', $3^{rd}$ edition, ed. March, J., John Wiley and Sons, New York, 1985).

Compounds of formula (I) thus also include the tautomer forms of formula:

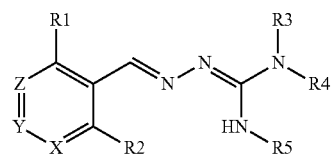

As an illustrative example, a tautomer form of example 1 is:

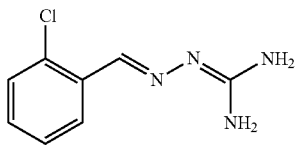 [SMILES: NC(N)=N/N=C/c1ccccc1Cl]

Compounds of the invention containing a chiral centre may be used as a racemic mixture, an enantiomerically enriched mixture, or the racemic mixture may be separated using well-known techniques and an individual enantiomer may be used alone.

Stereo and Geometric Isomers

Some of the compounds of the invention may exist as stereoisomers and/or geometric isomers—e.g. they may possess one or more asymmetric and/or geometric centres and so may exist in two or more stereoisomeric and/or geometric forms. The present invention contemplates the use of all the individual stereoisomers and geometric isomers of those inhibitor agents, and mixtures thereof. The terms used in the claims encompass these forms, provided said forms retain the appropriate functional activity (though not necessarily to the same degree).

The present invention also includes all suitable isotopic variations of the agent or a pharmaceutically acceptable salt thereof. An isotopic variation of an agent of the present invention or a pharmaceutically acceptable salt thereof is defined as one in which at least one atom is replaced by an atom having the same atomic number but an atomic mass different from the atomic mass usually found in nature. Examples of isotopes that can be incorporated into the agent and pharmaceutically acceptable salts thereof include isotopes of hydrogen, carbon, nitrogen, oxygen, phosphorus, sulfur, fluorine and chlorine such as $^2H$, $^3H$, $^{13}C$, $^{14}C$, $^{16}N$, $^{17}O$, $^{18}O$, $^{31}P$, $^{32}P$, $^{35}S$, $^{18}F$ and $^{36}Cl$, respectively. Certain isotopic variations of the agent and pharmaceutically acceptable salts thereof, for example, those in which a radioactive isotope such as $^3H$ or $^{14}C$ is incorporated, are useful in drug and/or substrate tissue distribution studies. Tritiated, i.e., $^3H$, and carbon-14, i.e., $^{14}C$, isotopes are particularly preferred for their ease of preparation and detectability. Further, substitution with isotopes such as deuterium, i.e., $^2H$, may afford certain therapeutic advantages resulting from greater metabolic stability, for example, increased in vivo half-life or reduced dosage requirements and hence may be preferred in some circumstances. For example, the invention includes compounds of general formula (I) where any hydrogen atom has been replaced by a deuterium atom. Isotopic variations of the agent of the present invention and pharmaceutically acceptable salts thereof of this invention can generally be prepared by conventional procedures using appropriate isotopic variations of suitable reagents.

Prodrugs

The invention further includes the compounds of the present invention in prodrug form, i.e. covalently bonded compounds which release the active parent drug according to general formula (I) in vivo. Such prodrugs are generally compounds of the invention wherein one or more appropriate groups have been modified such that the modification may be reversed upon administration to a human or mammalian subject. Reversion is usually performed by an enzyme naturally present in such subject, though it is possible for a second agent to be administered together with such a prodrug in order to perform the reversion in vivo. Examples of such modifications include ester (for example, any of those described above), wherein the reversion may be carried out be an esterase etc. Other such systems will be well known to those skilled in the art.

Solvates

The present invention also includes solvate forms of the compounds of the present invention. The terms used in the claims encompass these forms.

Polymorphs

The invention further relates to the compounds of the present invention in their various crystalline forms, polymorphic forms and (an)hydrous forms. It is well established within the pharmaceutical industry that chemical compounds may be isolated in any of such forms by slightly varying the method of purification and or isolation form the solvents used in the synthetic preparation of such compounds.

Administration

The pharmaceutical compositions of the present invention may be adapted for rectal, nasal, intrabronchial, topical (including buccal, sublingual and ophthalmic administration, in particular for intra-ocular, intra-vitreal, topical ocular or peri-ocular administration), vaginal or parenteral (including subcutaneous, intramuscular, intravenous, intraarterial and intradermal), intraperitoneal or intrathecal administration. Preferably the formulation is an orally administered formulation. The formulations may conveniently be presented in unit dosage form, i.e., in the form of discrete portions containing a unit dose, or a multiple or sub-unit of a unit dose. By way of example, the formulations may be in the form of tablets and sustained release capsules, and may be prepared by any method well known in the art of pharmacy.

Formulations for oral administration in the present invention may be presented as: discrete units such as capsules, gellules, drops, cachets, pills or tablets each containing a predetermined amount of the active agent; as a powder or granules; as a solution, emulsion or a suspension of the active agent in an aqueous liquid or a non-aqueous liquid; or as an oil-in-water liquid emulsion or a water-in-oil liquid emulsion; or as a bolus etc. Preferably, these compositions contain from 1 to 250 mg, more preferably from 10-100 mg, and more preferably from 1-100 mg, of active ingredient per dose.

For compositions for oral administration (e.g. tablets and capsules), the term "acceptable carrier" includes vehicles such as common excipients e.g. binding agents, for example syrup, acacia, gelatin, sorbitol, tragacanth, polyvinylpyrrolidone (Povidone), methylcellulose, ethylcellulose, sodium carboxymethylcellulose, hydroxypropylmethylcellulose, sucrose and starch; fillers and carriers, for example corn starch, gelatin, lactose, sucrose, microcrystalline cellulose, kaolin, mannitol, dicalcium phosphate, sodium chloride and alginic acid; and lubricants such as magnesium stearate, sodium stearate and other metallic stearates, glycerol stearate stearic acid, silicone fluid, talc waxes, oils and colloidal silica. Flavouring agents such as peppermint, oil of wintergreen, cherry flavouring and the like can also be used. It may be desirable to add a colouring agent to make the dosage form readily identifiable. Tablets may also be coated by methods well known in the art.

A tablet may be made by compression or moulding, optionally with one or more accessory ingredients. Compressed tablets may be prepared by compressing in a suitable machine the active agent in a free flowing form such as a powder or granules, optionally mixed with a binder, lubricant, inert diluent, preservative, surface-active or dispersing agent. Moulded tablets may be made by moulding in a suitable machine a mixture of the powdered compound moistened with an inert liquid diluent. The tablets may be optionally be coated or scored and may be formulated so as to provide slow or controlled release of the active agent.

Other formulations suitable for oral administration include lozenges comprising the active agent in a flavoured base, usually sucrose and acacia or tragacanth; pastilles comprising the active agent in an inert base such as gelatin and glycerin, or sucrose and acacia; and mouthwashes comprising the active agent in a suitable liquid carrier.

Other forms of administration comprise solutions or emulsions which may be injected intravenously, intraarterially, intrathecally, subcutaneously, intradermally, intraperitoneally, intra-ocularly, topical, peri-ocularly or intramuscularly, and which are prepared from sterile or sterilisable solutions.

The pharmaceutical compositions of the present invention may also be in form of suppositories, pessaries, suspensions, emulsions, lotions, ointments, creams, gels, sprays, solutions or dusting powders.

An alternative means of transdermal administration is by use of a skin patch. For example, the active ingredient can be incorporated into a cream consisting of an aqueous emulsion of polyethylene glycols or liquid paraffin. The active ingredient can also be incorporated, at a concentration of between 1 and 10% by weight, into an ointment consisting of a white wax or white soft paraffin base together with such stabilisers and preservatives as may be required.

Dosage

A person of ordinary skill in the art can easily determine an appropriate dose of one of the instant compositions to administer to a subject without undue experimentation. Typically, a physician will determine the actual dosage which will be most suitable for an individual patient and it will depend on a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy. The dosages disclosed herein are exemplary of the average case. There can of course be individual instances where higher or lower dosage ranges are merited, and such are within the scope of this invention.

In accordance with this invention, an effective amount of a compound of general formula (I) may be administered to target a particular condition or disease. Of course, this dosage amount will further be modified according to the type of administration of the compound. For example, to achieve an "effective amount" for acute therapy, parenteral administration of a compound of general formula (I) is preferred. An intravenous infusion of the compound in 5% dextrose in water or normal saline, or a similar formulation with suitable excipients, is most effective, although an intramuscular bolus injection is also useful. Typically, the parenteral dose will be about 0.01 to about 100 mg/kg; preferably between 0.1 and 20 mg/kg, in a manner to maintain the concentration of drug in the plasma at an effective concentration The compounds may be administered one to four times daily at a level to achieve a total daily dose of about 0.4 to about 400 mg/kg/day. The precise amount of an inventive compound which is therapeutically effective, and the route by which such compound is best administered, is readily determined by one of ordinary skill in the art by comparing the blood level of the agent to the concentration required to have a therapeutic effect.

The compounds of this invention may also be administered orally to the patient, in a manner such that the concentration of drug is sufficient to achieve one or more of the therapeutic indications disclosed herein. Typically, a pharmaceutical composition containing the compound is administered at an oral dose of between about 0.1 to about 50 mg/kg in a manner consistent with the condition of the patient. Preferably the oral dose would be about 0.1 to about 20 mg/kg.

No unacceptable toxicological effects are expected when compounds of the present invention are administered in accordance with the present invention. The compounds of this invention, which may have good bioavailability, may be tested in one of several biological assays to determine the concentration of a compound which is required to have a given pharmacological effect.

Combinations

In a particularly preferred embodiment, the one or more compounds of the invention are administered in combination with one or more other active agents, for example, existing drugs available on the market. In such cases, the compounds of the invention may be administered consecutively, simultaneously or sequentially with the one or more other active agents.

Drugs in general are more effective when used in combination. In particular, combination therapy is desirable in order to avoid an overlap of major toxicities, mechanism of action and resistance mechanism(s). Furthermore, it is also desirable to administer most drugs at their maximum tolerated doses with minimum time intervals between such doses. The major advantages of combining drugs are that it may promote additive or possible synergistic effects through biochemical interactions and also may decrease the emergence of resistance.

Beneficial combinations may be suggested by studying the inhibitory activity of the test compounds with agents known or suspected of being valuable in the treatment of a particular disorder. This procedure can also be used to determine the order of administration of the agents, i.e. before, simultaneously, or after delivery. Such scheduling may be a feature of all the active agents identified herein.

According to preferred embodiment, the invention relates to a pharmaceutical composition comprising a PPP1R15A inhibitor of formula (I) or a pharmaceutical acceptable salt thereof, and a compound increasing the expression and/or the activity of protein BiP and a pharmaceutically acceptable carrier and/or excipient (see WO2013/124484). Preferably, the compound increasing the expression and/or activity of protein BiP is selected from the group consisting of valproic acid or a derivative thereof, trichostatin A, lithium, I-(3,4-dihydroxy-phenyl)-2-thiocyanate-ethanone, and exendin-4. According to a preferred embodiment the protein BiP is valproic acid or a derivative thereof such as 2-ene-valproic acid.

According to a preferred embodiment, the invention relates to a pharmaceutical composition comprising a PPP1R15A inhibitor of formula (I) or a pharmaceutical acceptable salt thereof, and a compound increasing the expression and/or the activity of protein BiP and a pharmaceutically acceptable carrier and/or excipient, to treat a disorder associated with the PPP1R15A pathway and associated with protein misfolding stress and in particular with accumulation of misfolded proteins. Preferably, the disease is selected in the group of tauopathies, synucleinopathies, polyglutamine and polyalanine diseases, leukodystrophies, charcot-marie-tooth diseases, seipinopathies, cystic fibrosis, multiple sclerosis, lysosomal storage disorders, amyloidosis diseases, retinal diseases, inflammation, metabolic disorders, cardio-vascular disorders, osteoporosis, nervous system trauma, ischemia.

Assay

A further aspect of the invention relates to the use of a compound as described above in an assay for identifying further candidate compounds capable of inhibiting PPP1R15A-PP1.

Preferably, the assay is a competitive binding assay. More preferably, the competitive binding assay comprises contacting a compound of the invention with PPP1R15A-PP1 and a candidate compound and detecting any change in the interaction between the compound according to the invention and the PPP1R15A-PP1.

Preferably, the candidate compound is generated by conventional SAR modification of a compound of the invention. As used herein, the term "conventional SAR modification" refers to standard methods known in the art for varying a given compound by way of chemical derivatisation.

Thus, in one aspect, the identified compound may act as a model (for example, a template) for the development of other compounds. The compounds employed in such a test may be free in solution, affixed to a solid support, borne on a cell surface, or located intracellularly. The abolition of activity or the formation of binding complexes between the compound and the agent being tested may be measured.

The assay of the present invention may be a screen, whereby a number of agents are tested. In one aspect, the assay method of the present invention is a high through-put screen.

This invention also contemplates the use of competitive drug screening assays in which neutralising antibodies capable of binding a compound specifically compete with a test compound for binding to a compound.

Another technique for screening provides for high throughput screening (HTS) of agents having suitable binding affinity to the substances and is based upon the method described in detail in WO 84/03564.

It is expected that the assay methods of the present invention will be suitable for both small and large-scale screening of test compounds as well as in quantitative assays.

Preferably, the competitive binding assay comprises contacting a compound of the invention with PPP1R15A-PP1 in the presence of a known substrate of PPP1R15A-PP1 and detecting any change in the interaction between said PPP1R15A-PP1 and said known substrate.

A further aspect of the invention provides a method of detecting the binding of a ligand to PPP1R15A-PP1, said method comprising the steps of:
(i) contacting a ligand with PPP1R15A-PP1 in the presence of a known substrate;
(ii) detecting any change in the interaction between PPP1R15A-PP1 and said known substrate;
and wherein said ligand is a compound of the invention.

One aspect of the invention relates to a process comprising the steps of:
(a) performing an assay method described hereinabove;
(b) identifying one or more ligands capable of binding to a ligand binding domain; and
(c) preparing a quantity of said one or more ligands.

Another aspect of the invention provides a process comprising the steps of:
(a) performing an assay method described hereinabove;
(b) identifying one or more ligands capable of binding to a ligand binding domain; and
(c) preparing a pharmaceutical composition comprising said one or more ligands.

Another aspect of the invention provides a process comprising the steps of:
(a) performing an assay method described hereinabove;
(b) identifying one or more ligands capable of binding to a ligand binding domain;
(c) modifying said one or more ligands capable of binding to a ligand binding domain;
(d) performing the assay method described hereinabove;
(e) optionally preparing a pharmaceutical composition comprising said one or more ligands.

The invention also relates to a ligand identified by the method described hereinabove.

Yet another aspect of the invention relates to a pharmaceutical composition comprising a ligand identified by the method described hereinabove.

Another aspect of the invention relates to the use of a ligand identified by the method described hereinabove in the preparation of a pharmaceutical composition for use in the treatment of a disorder associated with accumulation of misfolded proteins as defined above.

The above methods may be used to screen for a ligand useful as an inhibitor of PPP1R15A-PP1.

Compounds of general formula (I) are useful both as laboratory tools and as therapeutic agents. In the laboratory certain compounds of the invention are useful in establishing whether a known or newly discovered target contributes a critical or at least significant biochemical function during the establishment or progression of a disease state, a process commonly referred to as 'target validation'.

The present invention is further described with reference to the following figures wherein.

Figure 6:
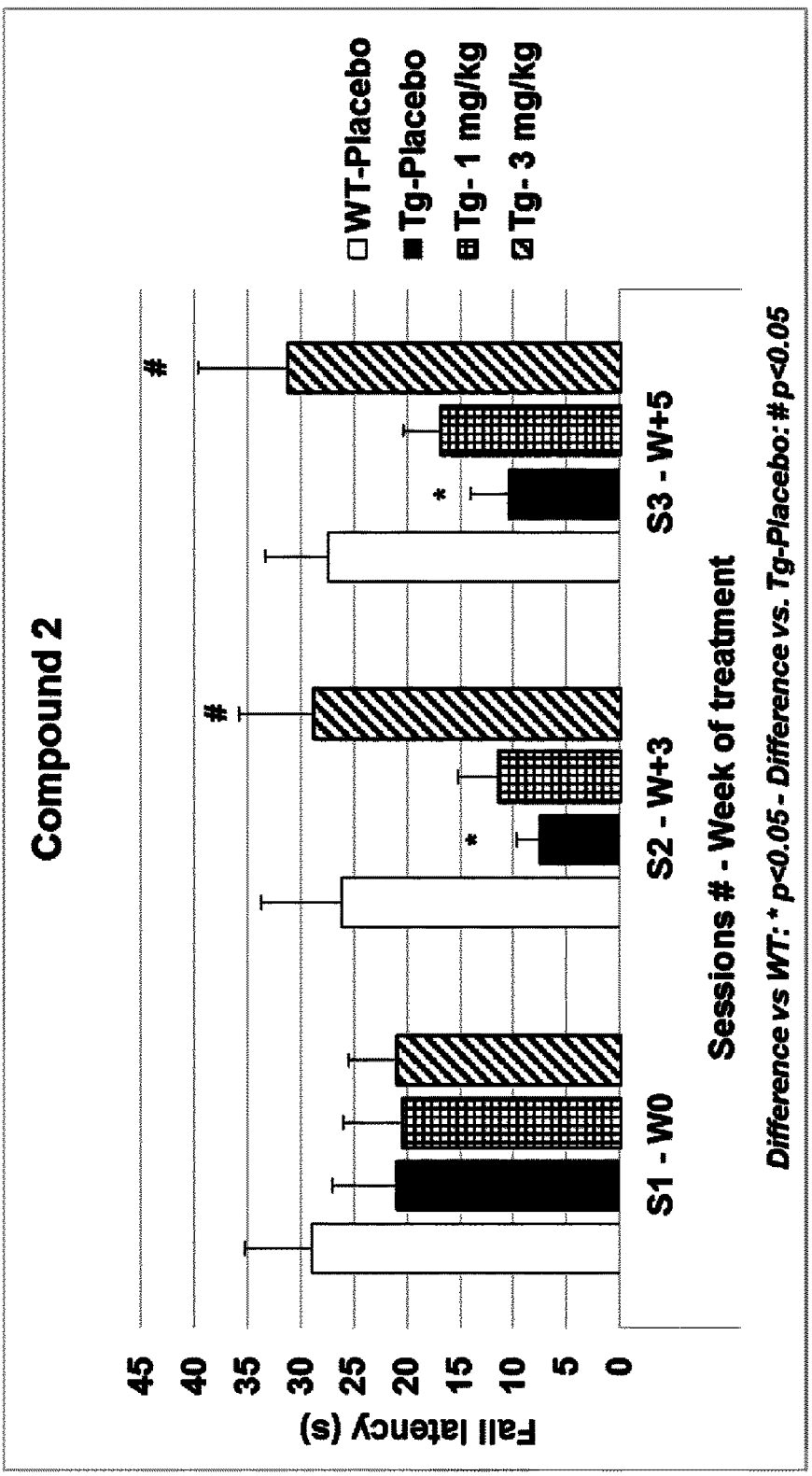

IFB-B: Compound 2 is administered orally.
BID: administration twice a day
QD: administration one a day FIG. 6 shows the ability of compound 2 at different concentrations and regimen to prevent motor defects of CMT-1A in PMP-22 in transgenic (TG) rat over-expressing PMP-22. Compound 2 is administered orally once a day.

Figure 7:
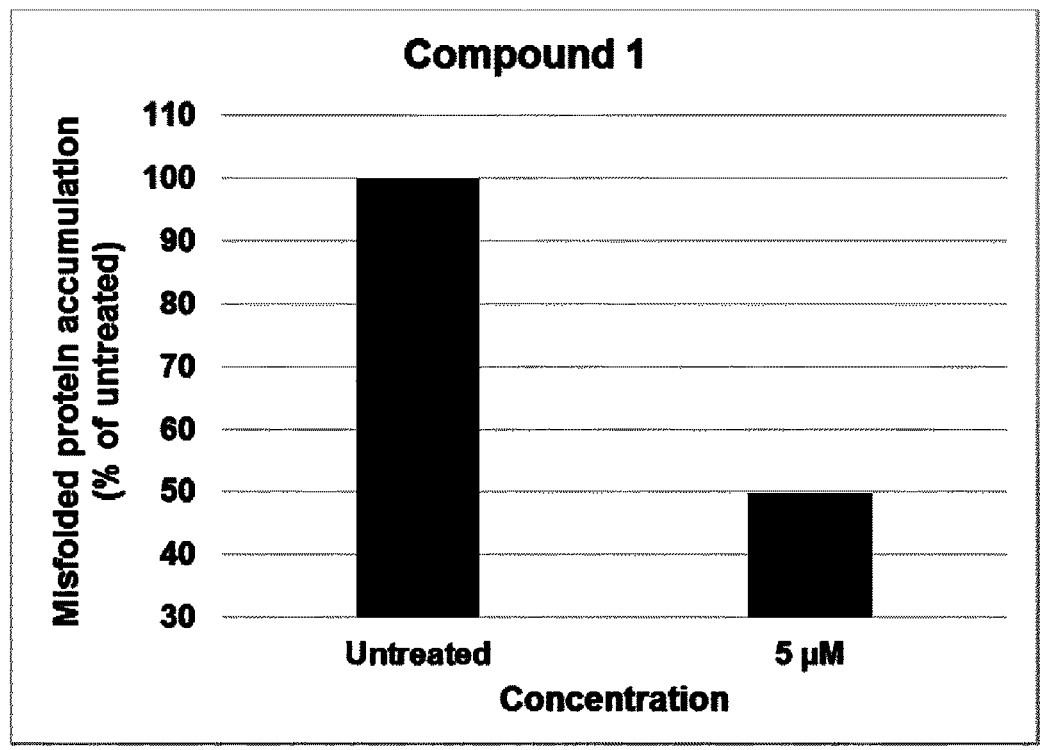

FIG. 7 shows the ability of compound 1 at 5 microM to prevent the accumulation of T181P mutated DM20 protein in Human 293T cell.

Figure 8:
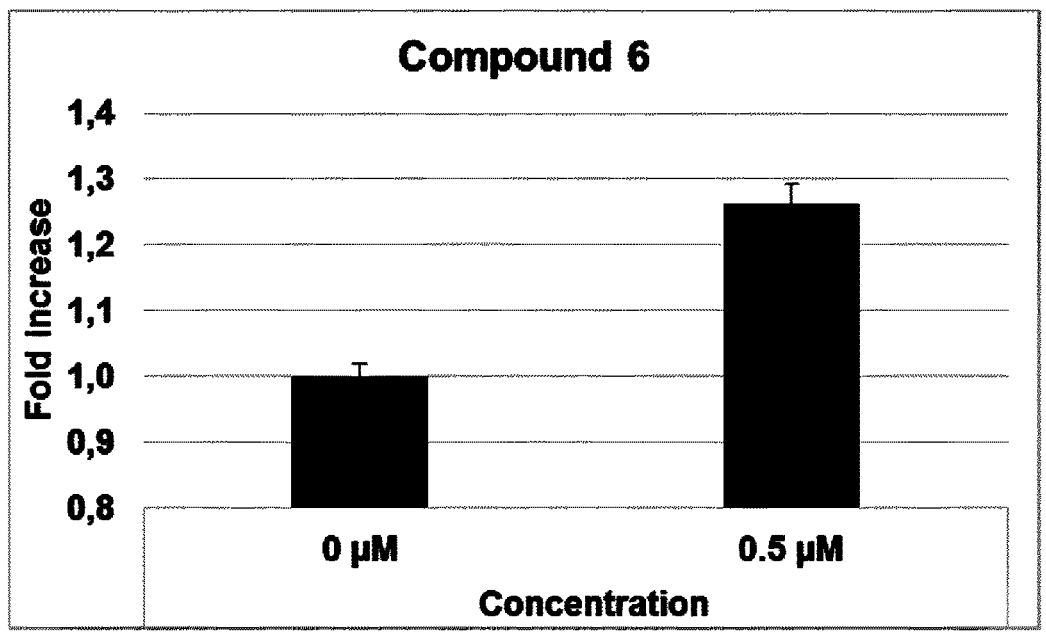

FIG. 8 shows the ability of compounds 6 to prevent cell death associated with the accumulation of misfold prone Insulin Akita expressed in Min6 cells.

Figure 9:
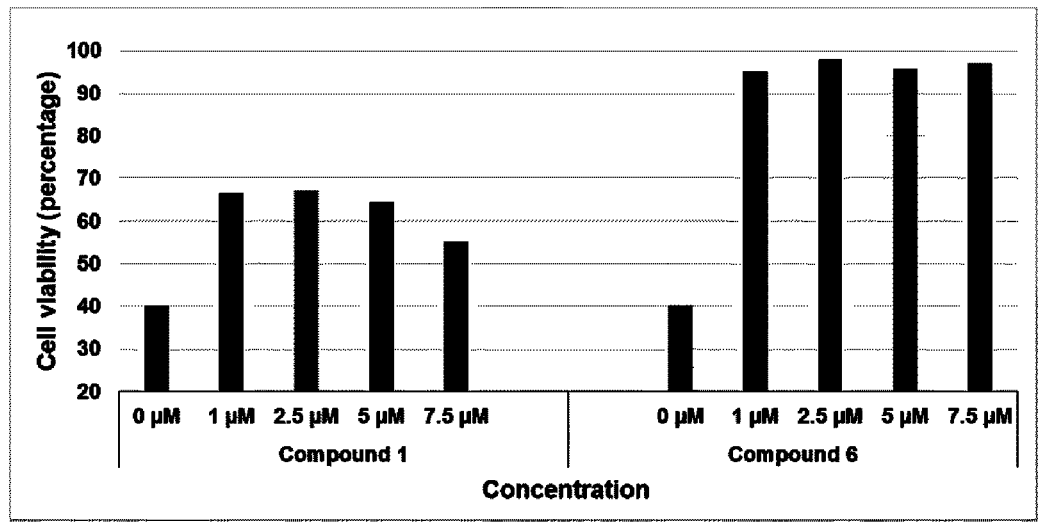

FIG. 9 shows the ability of compound 1 and compound 6 at different concentrations to prevent Min6 insulinoma cell death associated with accumulation of misfolded protein induced by 6 hour exposure to tunicamycin.

Figure 10:
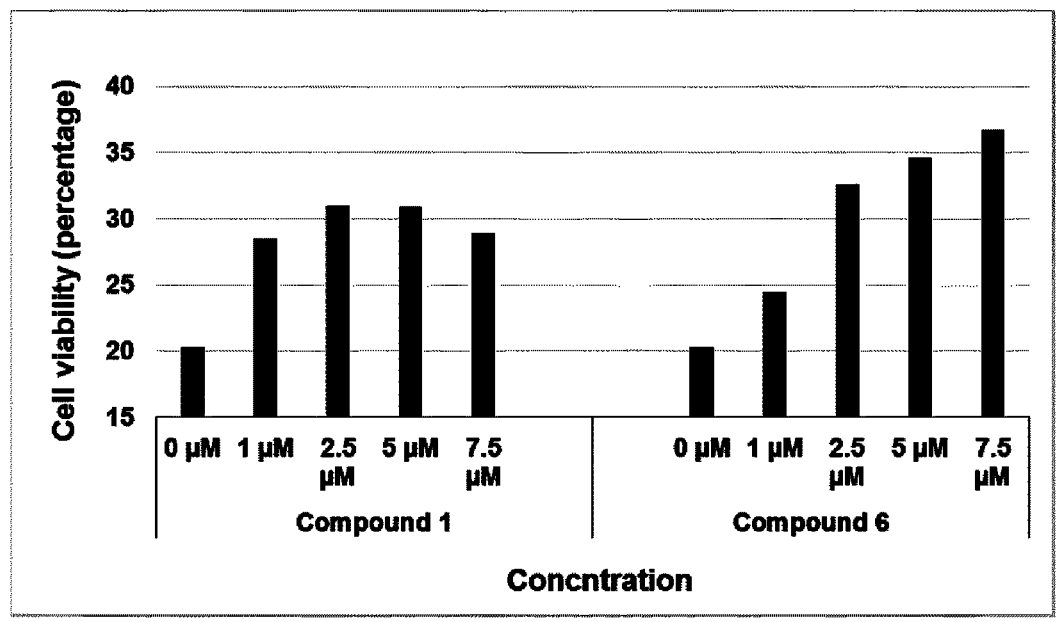

FIG. 10 shows the ability of compound 1 and compound 6 at different concentrations to prevent INS1 insulinoma cell death associated with accumulation of misfolded protein induced by 6 hour exposure to tunicamycin.

Figure 11:
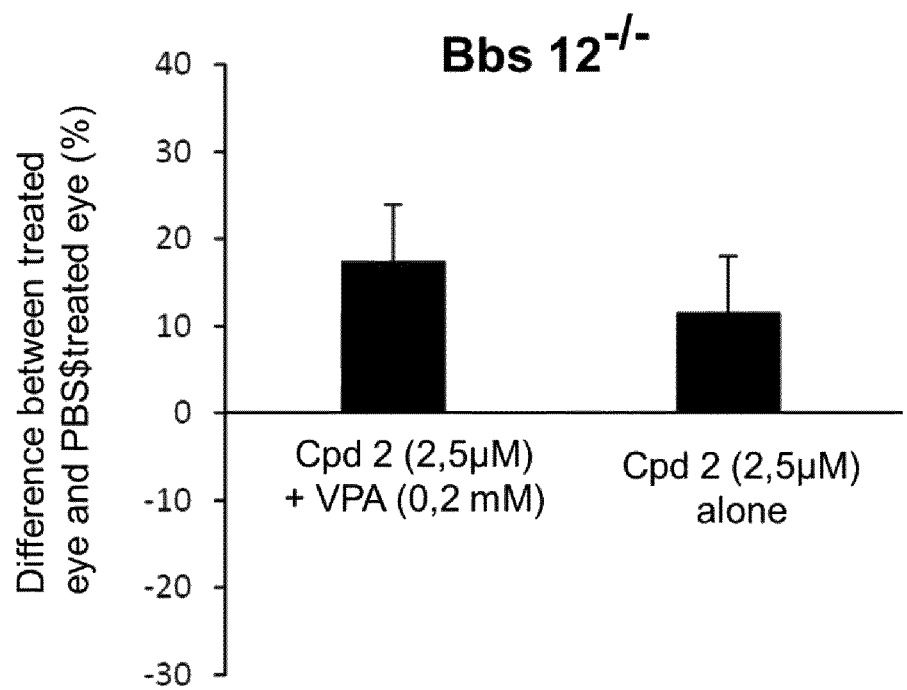

FIG. 11 shows the ability of compound 2 to protect photoreceptors against apoptosis and preserves light detection in BBS12−/− mice. Electroretinogram (ERG). Tabulated mean of the percentage different between BBS12−/− eye with compound 2 (2.5 microM) in association with Valproic acid (0.2 mM) or compound 2 (2.5 microM) alone versus the vehicle-treated eye (PBS). Positive translates an increase in ERG response and negative translates a decrease in ERG compare to the PBS treated eye. n=10-14 per group.

Figure 12:
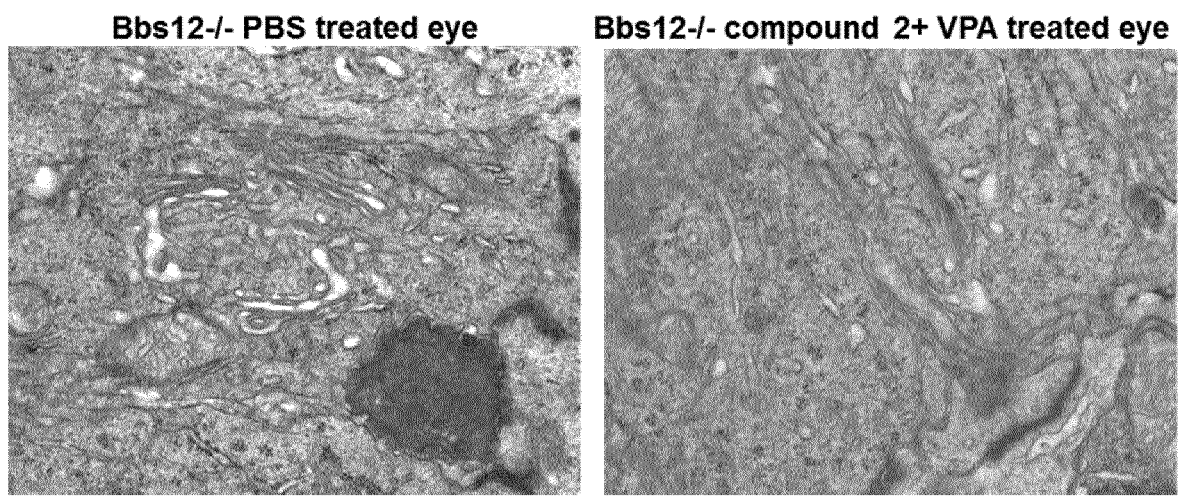

FIG. 12 shows the ability of compound 2 to decrease protein load in the Endoplasmic Reticulum in BBS12−/− mice. Transmission Electronic Microscopy (TEM) endoplasmic reticulum (ER) of BBS12−/− photoreceptors in response to the administration of Compound 2 (2.5 microM) in combination with ValproIc acid (VPA) (0.2 mM) or PBS. Dilatation of the ER cisternaes is observed when PBS only is injected (left) whereas Compound 2 in combination with VPA are able to decrease this dilatation (right) after one single intra-vitreal injection.

Figure 13:
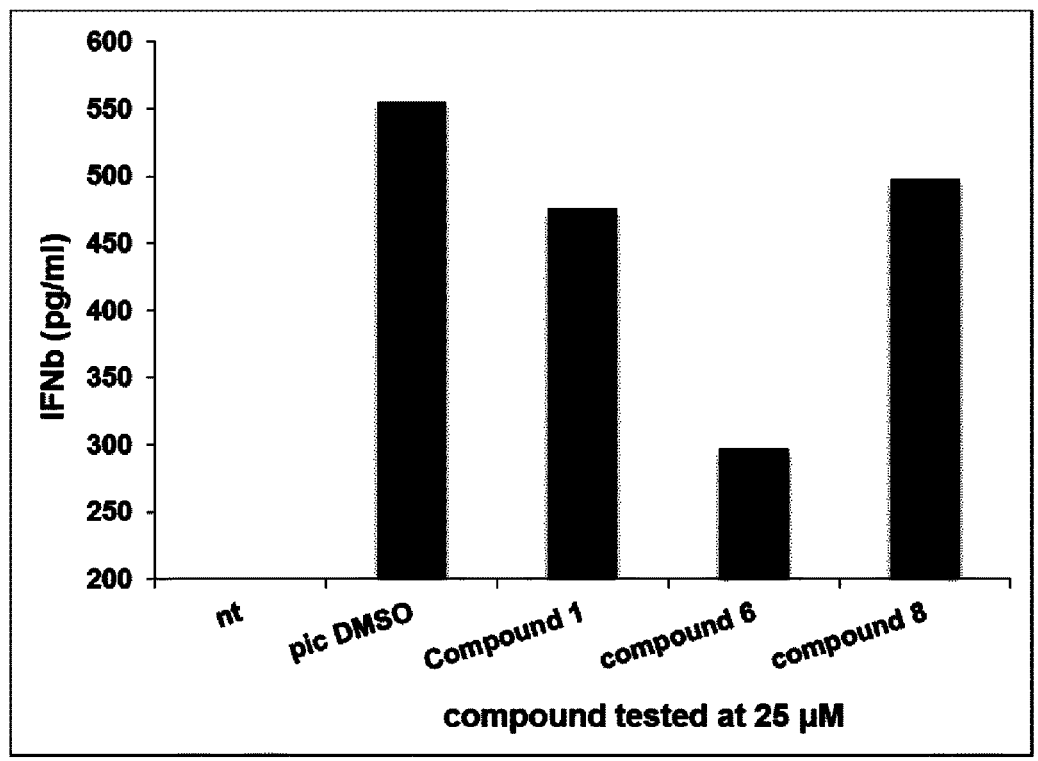

FIG. 13 shows the ability of compounds 1, 6 and 8 (at 25 microM) to prevent type-I Interferon production by mouse embryonic fibroblasts lipofected with poly I:C.

Figure 14:
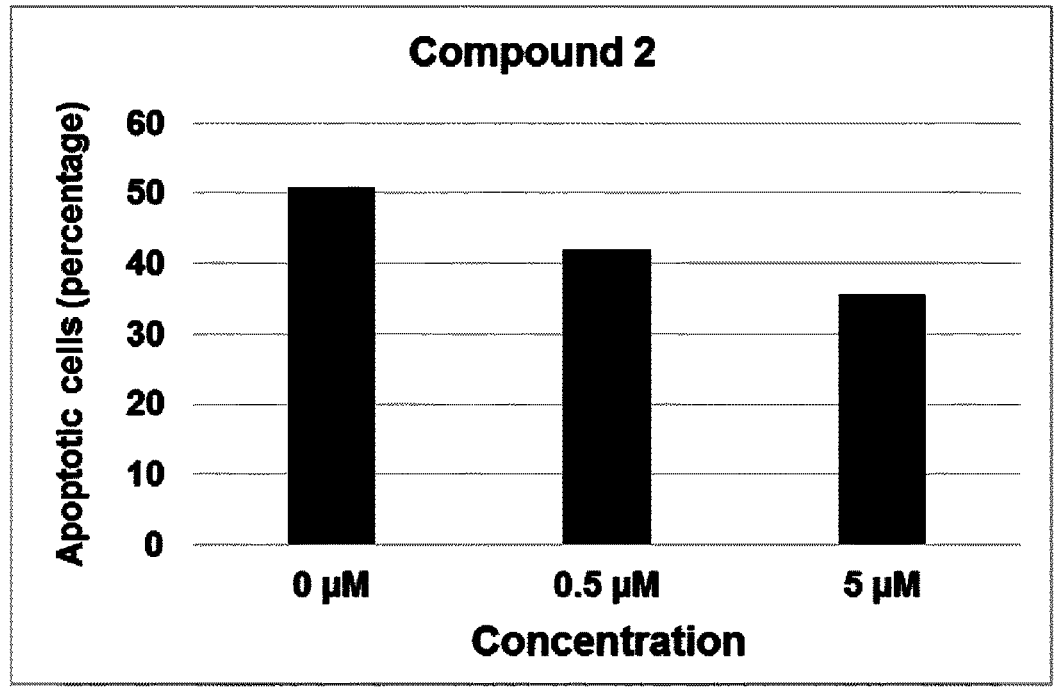

FIG. 14 shows the ability of Compound 2 to protect neonatal rat cardiomyocytes against hypoxia-induced apoptosis. The graph shows the percentage of apoptotic cells measured by FACS analysis. Cardiomyocytes were exposed to hypoxia (0.3% $O_2$) for 36 h in the absence (0 μM) or in the presence of indicated concentrations of Compound 2 (n=3).

The present invention is further described with reference to the following non-limiting examples.

EXAMPLES

1—Materials & Methods
Compound 3 was purchased from Chembridge ref: 5173161
Compound 4 was purchased from Chemdiv ref: 0589-0012
Compound 5 was purchased from Chemdiv ref: 1683-6502
1.1—Preparation of the Compounds According to the Present Invention The reactants and commercials compounds were purchased from Acros Organics, Sigma-Aldrich. The compounds according to the present invention can be prepared according to the following general procedure:

General Procedure A:

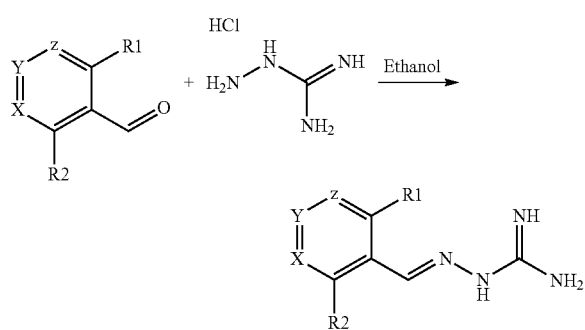

To a solution of benzaldehyde (1 eq.) in ethanol (300 ml) was sequentially added Aminoguanidine hydrochloride (1 eq.) and sodium acetate (1 eq.) at 25° C. The resulting reaction mixture was heated at 80° C. for next ~6 hours. Reaction completion was monitored on TLC using dichloromethane/methanol (8/2) as mobile phase. After completion of reaction, the reaction mixture was allowed to cool down to 25° C. and dumped in the saturated solution of $NaHCO_3$ (700 ml). The resulting precipitate were filtered off under vacuum and washed with water (100 ml). The resulting solid material was titurated with diethylether (2×25 ml) and dried under vacuum to provide the desired substituted aminoguanidine derivative.

The following compounds were prepared according general procedure A:

Compound 1:
2-(2-chlorobenzylidene)hydrazinecarboximidamide

Prepared following general procedure A from 2-chlorobenzaldehyde (10 g) to give 11.1 g of desired compound (yield: 79.6%). $^1$H-NMR (DMSO-$d_6$): δ (ppm) 5.66 (s, 2H); 6.05 (s broad, 2H); 7.27 (m, 2H); 7.40 (m, 1H); 8.14 (dd, 1H); 8.27 (s, 1H); MS (ESI+): m/z=197.2 [M+H]$^+$.

Compound 2:
2-(2-chlorobenzylidene)hydrazinecarboximidamide acetate

To a suspension of 2-chlorobenzaldehyde (30.0 g) and Aminoguanidine bicarbonate (29.0 g) in Methanol (450 ml) was added Acetic acid (30 ml) at 25° C. The reaction mixture was stirred at 70° C. for 30 minutes. Reaction completion was monitored on TLC using Dichloromethane/Methanol (8/2) as mobile phase. After completion of reaction, the reaction mixture was allowed to cool down to 25° C. and concentrated under vacuum. The residue was suspended in methanol (250 ml) and insoluble material was removed by flirtation. The resulting filtrate was concentrated under vacuum and the above mentioned process (suspension in methanol+filtration) was repeated for three more times. Then, the solid material was triturated with diethyl ether (3×100 ml) and dried under vacuum to provide 46.0 g of 2-(2-chlorobenzylidene)hydrazinecarboximidamide acetate Salt (yield: 84.2%) LC-MS: m/z=197.2 (M+H). $^1$H-NMR (DMSO-$d_6$): δ (ppm) 1.81 (s, 3H), 7.12 (m, 4H); 7.34 (m, 2H); 7.46 (m, 1H); 8.22 (m, 1H); 8.36 (s, 1H); LC-MS: m/z=197.2 [M+H]$^+$.

Compound 6: 2-[(3-chloropyridin-4-yl)methylidene]hydrazinecarboximidamide

Prepared following general procedure A from 2-chlorobenzaldehyde (0.5 g) to give 0.16 g of desired compound (yield: 23%). $^1$H-NMR (DMSO-$d_6$): δ (ppm) 6.00 (s broad, 2H); 6.32 (s broad, 2H); 8.10 (d, 1H); 8.14 (s, 1H); 8.35 (dd, 1H); 8.52 (s, 1H); MS (ESI+): m/z=198.0 [M+H]$^+$.

Compound 7: 2-[(3-chloropyridin-4-yl)methylidene]hydrazinecarboximidamide acetate To a suspension of 3-chloroisonicotinaldehyde (2.0 g) and aminoguanidine bicarbonate (2.12 g) in methanol (28 ml) was added acetic acid (2 ml) at 25° C. The reaction mixture was stirred at 70° C. for ~2 hours. Reaction completion was monitored on TLC using Dichloromethane/Methanol (8/2) as mobile phase. After completion of reaction, the crude mixture were allowed to cool down to 25° C. and concentrated under vacuum. The solid material was triturated with methanol:diethyl ether (9:1) (4×50 ml) and dried under vacuum to 2.0 g of 2-[(3-chloropyridin-4-yl)methylidene]hydrazinecarboximidamide acetate salt (yield: 55.1%). $^1$H-NMR (DMSO-d$_6$): δ (ppm) 6.01 (brs, 2H); 6.48 (m, 4H); 8.12 (d, 1H); 8.16 (s, 1H); 8.38 (dd, 1H); 8.54 (s, 1H); MS (ESI+): m/z=198.1 [M+H]$^+$.

Compound 8: 2-(2-chloro-6-fluorobenzylidene)hydrazinecarboximidamide acetate

To a suspension of 2-chloro-6-fluorobenzaldehyde (1.5 g) and aminoguanidine bicarbonate (1.29 g) in methanol (22 ml) was added acetic acid (1.5 ml) at 25° C. The reaction mixture was stirred at 70° C. for ~1 hour. Reaction completion was monitored on TLC using Dichloromethane/Methanol (8/2) as mobile phase. After completion of reaction, the mixture was allowed to cool down to 25° C. and concentrated under vacuum. The resulting solid material was triturated with methanol:diethyl ether (9:1) (3×50 ml) and dried under vacuum to give 2.2 g 2-(2-chloro-6-fluorobenzylidene)hydrazinecarboximidamide acetate Salt (yield: 84.8%). $^1$H-NMR (DMSO-d$_6$): δ (ppm) 1.89 (s, 3H), 6.13 (s broad, 4H); 7.24 (m, 1H); 7.33 (m, 2H) 8.17 (s, 1H); MS (ESI+): m/z=215.1 [M+H]$^+$.

Compound 9: 2-(2-chloro-4-methylbenzylidene)hydrazinecarboximidamide

Prepared following general procedure A from 2-chloro-4-methylbenzaldehyde (0.2 g) to give 255 mg of desired compound (yield: 93.8%). $^1$H-NMR (DMSO-d$_6$): δ (ppm) 2.29 (s, 3H); 5.60 (s broad, 2H); 6.00 (s broad, 2H); 7.10 (d, 2H); 7.27 (s, 1H); 8.02 (d, 1H); 8.24 (s, 1H); MS (ESI+): m/z=210.9 [M+H]$^+$.

Compound 10: 2-(2-chloro-5-methylbenzylidene)hydrazinecarboximidamide

Prepared following general procedure A from 2-chloro-5-methylbenzaldehyde (0.2 g) to give 156 mg of desired compound (yield: 57.4%). $^1$H-NMR (DMSO-d$_6$): δ (ppm) 2.30 (s, 3H); 5.64 (s broad, 2H); 6.06 (s broad, 2H); 7.07 (d, 2H); 7.27 (d, 1H); 7.97 (s, 1H); 8.24 (s, 1H); MS (ESI+): m/z=210.9 [M+H]$^+$.

Compound 11: 2-(2-chloro-3-methylbenzylidene)hydrazinecarboximidamide

Prepared following general procedure A from 2-chloro-3-methylbenzaldehyde (0.2 g) to give 226 mg of desired compound (yield: 83.1%). $^1$H-NMR (DMSO-d$_6$): δ (ppm) 2.17 (s, 3H); 5.64 (s broad, 2H); 6.03 (s broad, 2H); 7.18 (t, 2H); 7.24 (d, 1H); 7.99 (s, 1H); 8.37 (s, 1H); MS (ESI+): m/z=210.9 [M+H]$^+$.

Selected compounds according to the invention are set forth in Table 1 below:

| Compound Number | Structure | Chemical Name |
| --- | --- | --- |
| Compound 1 | 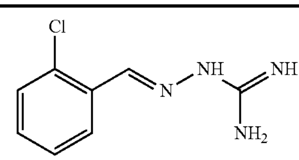 | 2-(2-chlorobenzylidene)hydrazinecarboximidamide |
| Compound 2 | 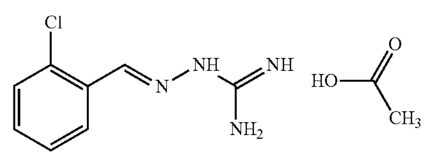 | 2-(2-chlorobenzylidene)hydrazinecarboximidamide acetate |
| Compound 3 | 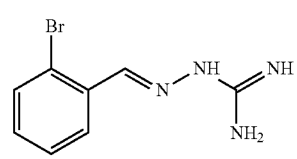 [SMILES: N=C(N)N/N=C/c1ccccc1Br] | 2-(2-bromobenzylidene)hydrazinecarboximidamide |
| Compound 4 | 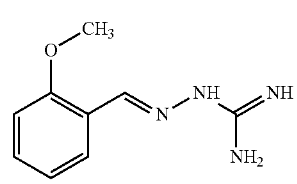 | 2-(2-methoxybenzylidene)hydrazinecarboximidamide |
| Compound 5 | 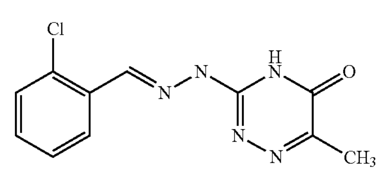 [SMILES: Cc1nnc(N/N=C/c2ccccc2Cl)[nH]c1=O] | 3-{[(2-chlorobenzylidene)amino]methyl}-6-methyl-1,2,4-triazin-5(4H)-one |

| Compound Number | Structure | Chemical Name |
|---|---|---|
| Compound 6 | 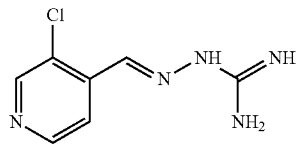 [SMILES: N=C(N)N/N=C/c1ccncc1Cl] | 2-[(3-chloropyridin-4-yl)methylidene]hydrazinecarboximidamide |
| Compound 7 | 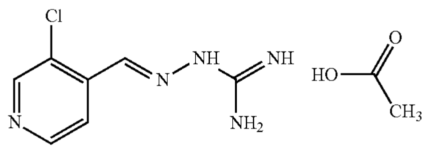 | 2-[(3-chloropyridin-4-yl)methylidene]hydrazinecarboximidamide acetate |
| Compound 8 | 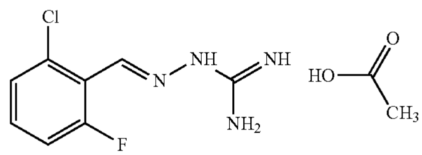 | 2-(2-chloro-6-fluorobenzylidene)hydrazinecarboximidamide acetate |
| Compound 9 | 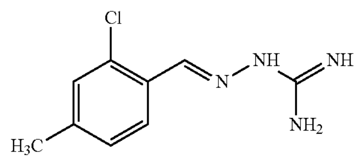 | 2-(2-chloro-4-methylbenzylidene)hydrazinecarboximidamide |
| Compound 10 | 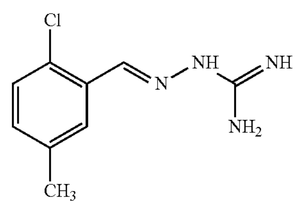 | 2-(2-chloro-5-methylbenzylidene)hydrazinecarboximidamide |
| Compound 11 | 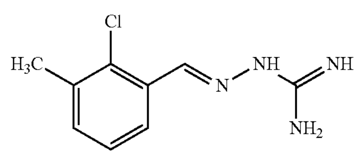 | 2-(2-chloro-3-methylbenzylidene)hydrazinecarboximidamide |

In some of the experiments below, the salt of these compounds may be used.

1.2—Mammalian Cell Culture, Constructs and Transfection

HeLa Cells were cultured in Eagle's Minimum Essential Medium (EMEM) supplemented with Glutamine, Sodium Pyruvate, Non-Essential Amino Acids, Penicillin and Streptomycin (Lonza) containing 10% Fœtal Bovine Serum (FBS) (Biowest). 293T cells were cultured in Dubelcco's Modified Eagle's Media (DMEM) supplemented with penicillin, streptomycin, glutamine (Lonza) and 10% of fetal bovine serum (FBS) (Biowest).

Min6 cells were cultured in DMEM supplemented with penicillin, streptomycin, glutamine, sodium pyruvate, 50 μM β-Mercaptoethanol and 15% Fo et al Bovine Serum (FBS) (Biowest).

INS1 cells were cultured in RPMI supplemented with penicillin, streptomycin, glutamine, sodium pyruvate (Lonza), 50 μM β-ME and 10% of fetal bovine serum (FBS) (Biowest).

Each cell line was maintained at 37° C. in 5% $CO_2$ atmosphere.

Human open reading frame (ORF) sequences for PLP1, DM20 and Insulin were obtained from Life Technologies (Invitrogen) (IOH41689, IOH5252 and IOH7334 respectively). Construct cloning into the expression plasmid pDEST26 (Invitrogen) was performed by Gateway® LR Clonase™ II Enzyme Mix (Invitrogen). ORF mutations were carried out using the QuikChange Lightning Site-Directed Mutagenesis Kit (Stratagene) (T181P mutation for PLP1 and DM20 ORFs, Akita (C96Y) for Insulin ORF).

Gene expression into mammalian cells was carried out by nucleofection, using the Amaxa™ 4D-Nucleofector™ System (Lonza) or by transfection using Lipofectamine (Life technologies).

1.3—Cytoprotection from ER Stress

This assay is described in Tsaytler et al. (Science 2011).

HeLa Cells were cultured in Eagle's Minimum Essential Medium (EMEM) supplemented with Glutamine, Sodium Pyruvate, Non-Essential Amino Acids, Penicillin and Streptomycin containing 10% Fœtal Bovine Serum (FBS), at 37° C. in 5% $CO_2$ atmosphere. Cells were plated in 96 well plates at a density of 17,000 cells/mL the day before the treatment. ER stress was elicited by addition of 5 µg/mL tunicamycin (Sigma-Aldrich) together with the phosphatases inhibitors (0.5-10 µM). Media were changed 6 h later with fresh media and the cytoprotection was maintained by the addition of the phosphatases inhibitors (0.5-10 µM). Cell viability was assessed by measuring the reduction of WST-8 into formazan using Cell Counting Kit-8 (Sigma) according to the supplier's recommendation, 48 h or 72 h after tunicamycin treatment.

Cytoprotection from ER stress is measured in terms of cytoprotective potency effect compared to the reference compound Guanabenz (Tsaytler et al., Science 2011) after ER stress:

'−' no cytoprotective effect;
'+' lower cytoprotective effect compared to Guanabenz;
'++' similar cytoprotective effect compared to Guanabenz.

Table 1 summarizes the results of cytoprotective effect of different compounds of the invention, compared to guanabenz, after the stress induced by a 6 hour exposure of tunicamycin.

1.4—Assessment of Translation Rates in Unstressed Cells

HeLa cells (100,000 cells/ml) were plated in 6-well plates 24 h before each experiment and were either left untreated or treated with compounds (50 µM) for 2.5, 5 and 9 h. Culture medium was replaced by methionine-free DMEM medium (Invitrogen) 30 min before compounds addition. One hour before each time point, 50 µM of Click-iT® AHA (L-azidohomoalanine) (Invitrogen) was added to the culture medium in order to label newly synthesized proteins. At the end of each time point, cells were washed with ice-cold PBS and harvested by Trypsine dissociation (Lonza), then lysed in a 50 mM Tris-HCl buffer containing 1% of SDS (Sigma) and protease and phosphatase inhibitors (Sigma). Protein samples were coupled to alkyne biotin (Invitrogen) using Click-iT® Protein Reaction Buffer Kit (Invitrogen). Samples were denatured at 70° C. for 10 min, resolved on ECL 4-20% precasted gels (GE Healthcare) and transferred to nitrocellulose membranes (GE Healthcare). Alkyne biotin coupled to Click-iT® AHA incorporated to newly synthesized proteins was detected using streptavidin-HRP (Gentex). Revelation was performed by incubation of ECL Prime (GE Healthcare) and read by chemoluminiscence using Fusion Solo 3S (Vilber Lourmat).

1.5—Assessment of Translation Rates in Stressed Cells

Treatments were performed as for measuring translation in unstressed cells, except that Tunicamycin (5 µg/ml) was added together with the compounds.

1.6—Functional GPCR Assay for Adrenergic α2A Receptor (CellKey Detection Method)

The agonist activity of compounds was evaluated on CHO cells endogenously expressing human alpha2A receptor and was determined by measuring their effects on impedance modulation using the CellKey detection method.

Cells were seeded onto 96-well plate at density of 6×10$^4$ cells/well in HBSS buffer (Invitrogen)+20 mM HEPES (Invitrogen) with 0.1% BSA and are allowed to equilibrate for 60 min at 28° C. before the start of the experiment. Plates were placed onto the system and measurements were made at a temperature of 28° C. Solutions were added simultaneously to all 96 wells using an integrated fluidics system: HBSS (basal control), reference agonist at 100 nM (stimulated control), reference agonist ($EC_{50}$ determination) or the test compounds. Impedance measurements are monitored for 10 minutes after ligand addition. The standard reference agonist is epinephrine, which is tested in each experiment at several concentrations to generate a concentration-response curve from which its $EC_{50}$ value is calculated.

Dose-response data from test compounds were analysed with Hill software using non-linear regression analysis of the concentration-response curves generated with mean replicate values using Hill equation curve fitting. Results are presented table 1, compounds with EC50>33.3 µM are considered to have no significant alpha-2 adrenergic activity.

1.7—In Vitro Multiple Sclerosis Disease Model: Interferon-Gamma Injured Rat Oligodendrocytes Co-Cultured with Neurons Culture of Oligodendrocyte Co-Cultured with Neurons Neurons/OPC were cultured as previously describes by Yang et al. (2005 J Neurosci Methods; 149(1) pp 50-6) with modifications. Briefly, the full brain (without cerebellum) obtained from 17-day old rat embryos (Wistar, Janvier labs) were removed. The full brains were treated for 20 min at 37° C. with a trypsin-EDTA (Pan Biotech) solution at a final concentration of 0.05% trypsin and 0.02% EDTA. The dissociation was stopped by addition of Dulbecco's modified Eagle's medium (DMEM) with 4.5 g/liter of glucose (Pan Biotech), containing DNAse I grade II (final concentration 0.5 mg/ml; Pan Biotech, Batch: h140508) and 10% fetal calf serum (FCS; Invitrogen, Batch: 41Q7218K). Cells were mechanically dissociated by three forced passages through the tip of a 10-ml pipette. Cells were then centrifuged at 515 g for 10 min at 4° C. The supernatant was discarded, and the pellet was resuspended in a defined culture medium consisting of Neurobasal medium (Invitrogen, Batch: 1636133) with a 2% solution of B27 supplement (Invitrogen, Batch: 1660670), 2 mmol/liter of L-glutamine (Pan Biotech), 2% of PS solution, and, 1% of FCS and 10 ng/ml of platelet derived growth factor (PDGF-AA, Batch: H131205). The cells were seeded at a density of 20 000 cells per well in 96 well plates precoated with PLL (BD corning, Batch: 6614022) and laminine (Sigma, Batch: 083M4034V). The plates were maintained at 37° C. into a humidified incubator, in an atmosphere of air (95%)-CO2 (5%). Half of the medium was changed every 2 days with fresh medium. On days 18, test compounds were pre-incubated 1 hour before interferon-gamma (70 U/ml, 48H, R&D system, Batch: AAL2214081) application.

Test Compounds and Interferon-Gamma Exposure

On day 18 of culture, test compounds (4 concentrations) were solved in culture medium and then pre-incubated with oligodendrocyte co-cultured with neurons for 1 hour before the interferon-gamma (70 U/ml, 48H) application. One hour after test compounds incubation, interferon-gamma was added at 70 U/ml concentration for 48 H still in presence of test compounds. Then, cells were fixed by a cold solution of ethanol (95%, Sigma, Batch: SZBD3080V) and acetic acid (5%, Sigma, Batch: SZBD1760V) for 5 min at −20° C. After permeabilization with 0.1% of saponin (Sigma, Batch: BCBJ8417V), cells were incubated for 2 h with Monoclonal Anti-04 antibody produced in mouse (Sigma, batch: SLBF5997V) at dilution of 1/1000 in PBS (PAN, Batch: 8410813) containing 1% FCS, 0.1% saponin, for 2 h at room temperature. This antibody are revealed with Alexa Fluor 488 goat anti-mouse IgG (Invitrogen, batch: 1664729) at the dilution 1/400 in PBS containing 1% FCS, 0.1% saponin, for 1 h at room temperature.

Analysis of Total Number of 04 Cells

For each condition, 30 pictures per well were taken using ImageXpress (Molecular Device) with 20× magnification. All images were taken with the same conditions. Analysis of total number of 04 cells was performed automatically by using Custom module editor (Molecular Device). Data were expressed in percentage of control conditions (no intoxication, no interferon-gamma=100%) in order to express the interferon-gamma injury. All values were expressed as mean+/−SEM (s.e.mean) (n=6 wells per condition).

1.8—In Vitro Parkinson's Disease Model: Rotenone Injured Primary Mesencephalic Rat Neurons Culture of Mesencephalic Dopaminergic Neurons Rat dopaminergic neurons were cultured as described by Schinelli et al., (1988 J. Neurochem 50 pp 1900-07) and Visanji et al., (2008 FASEB J. 22(7) pp 2488-97). Briefly, the midbrains obtained from 15-day old rat embryos (Janvier Labs, France) were dissected under a microscope. The embryonic midbrains were removed and placed in ice-cold medium of Leibovitz (L15, Pan Biotech, Batch: 9310614) containing 2% of Penicillin-Streptomycin (PS, Pan Biotech, Batch: 1451013) and 1% of bovine serum albumin (BSA, Pan Biotech, Batch: h140603). The ventral portion of the mesencephalic flexure, a region of the developing brain rich in dopaminergic neurons, was used for the cell preparations.

The midbrains were dissociated by trypsinisation for 20 min at 37° C. (Trypsin 0.05% EDTA 0.02%, PanBiotech, Batch: 5890314). The reaction was stopped by the addition of Dulbecco's modified Eagle's medium (DMEM, PanBiotech, Batch: 1300714) containing DNAase I grade II (0.1 mg/ml, PanBiotech, Batch: H140508) and 10% of foetal calf serum (FCS, Gibco, Batch: 4107218K). Cells were then mechanically dissociated by 3 passages through a 10 ml pipette. Cells were then centrifuged at 180×g for 10 min at +4° C. on a layer of BSA (3.5%) in L15 medium. The supernatant was discarded and the cell pellets were resuspended in a defined culture medium consisting of Neurobasal (Invitrogen, Batch: 1636133) supplemented with B27 (2%, Invitrogen, Batch: 1660670), L-glutamine (2 mM, PanBiotech, Batch: 8150713) and 2% of PS solution and 10 ng/ml of Brain-derived neurotrophic factor (BDNF, PanBiotech, Batch: H140108) and 1 ng/ml of Glial-Derived Neurotrophic Factor (GDNF, Pan Biotech, Batch: H130917). Viable cells were counted in a Neubauer cytometer using the trypan blue exclusion test. The cells were seeded at a density of 40 000 cells/well in 96 well-plates pre-coated with poly-L-lysine (Corning Biocoat, Batch: 6614022) and maintained in a humidified incubator at 37° C. in 5% $CO_2$/95% air atmosphere. Half of the medium was changed every 2 days with fresh medium.

On day 6 of culture, the medium was removed and fresh medium was added, without or with rotenone (Sigma, Batch: 021M2227V) at 10 nM diluted in control medium, 3 wells per condition were assessed. Test compounds were solved in culture medium and then pre-incubated with mesencephalic neurons for 1 hour before the rotenone application.

After 24 hours of intoxication, cells were fixed by a solution of 4% paraformaldehyde (Sigma, batch SLBF7274V) in PBS (Pan Biotech, Batch: 4831114), pH=7.3 for 20 min at room temperature. The cells were washed again twice in PBS, and then were permeabilized and non-specific sites were blocked with a solution of PBS containing 0.1% of saponin (Sigma, batch: BCBJ8417V) and 1% FCS for 15 min at room temperature. Then, cells were incubated with Monoclonal Anti-Tyrosine Hydroxylase antibody produced in mouse (TH, Sigma, batch: 101M4796) at dilution of 1/10 000 in PBS containing 1% FCS, 0.1% saponin, for 2 h at room temperature. This antibody was revealed with Alexa Fluor 488 goat anti-mouse IgG (Molecular Probes, batch: 1531668) at the dilution 1/800 in PBS containing 1% FCS, 0.1% saponin, for 1 h at room temperature.

Analysis of Total Number of TH Positive Neurons

The immunolabeled cultures were automatically examined with ImageXpress (Molecular device USA). For each condition, 20 automatically fields per well (representing ~80% of the total surface of the well) from 3 wells were analyzed. The total number of TH neurons was automatically analyzed using Custom module editor (Molecular Devices, USA). Data were expressed in percentage of control conditions (no intoxication, no rotenone=100%) in order to express the rotenone injury. All values were expressed as mean+/−SEM (s.e. mean) of the 1 culture (n=3 wells per condition per culture).

1.9—In Vitro Alzheimer Disease Model: Amyloid-Beta 1-42 Injured Primary Cortical Rat Neurons.

Culture of Rat Cortical Neurons

Rat cortical neurons were cultured as described by Singer et al., (1999 J. Neuroscience 19 pp 2455-63) and Callizot et al., (2013 J. Neurosci. Res. 91 pp 706-16). Pregnant females (Wistar; Janvier Labs) at 15 days of gestation were killed by cervical dislocation. Fetuses were collected and immediately placed in ice-cold L15 Leibovitz medium (Pan Biotech, Batch: 9310614) with a 2% penicillin (10,000 U/ml) and streptomycin (10 mg/ml) solution (PS; Pan Biotech, Batch: 1451013) and 1% bovine serum albumin (BSA; Pan Biotech, Batch: h140603). Cortex was treated for 20 min at 37° C. with a trypsin-EDTA (Pan Biotech, Batch: 5890314) solution at a final concentration of 0.05% trypsin and 0.02% EDTA. The dissociation was stopped by addition of Dulbecco's modified Eagle's medium (DMEM) with 4.5 g/liter of glucose (Pan Biotech, batch: 1300714), containing DNAse I grade II (final concentration 0.5 mg/ml; Pan Biotech, Batch: h140508) and 10% fetal calf serum (FCS; Invitrogen, Batch: 41Q7218K). Cells were mechanically dissociated by three forced passages through the tip of a 10-ml pipette. Cells were then centrifuged at 515 g for 10 min at 4° C. The supernatant was discarded, and the pellet was resuspended in a defined culture medium consisting of Neurobasal medium (Invitrogen, Batch: 1636133) with a 2% solution of B27 supplement (Invitrogen, Batch: 1660670), 2 mmol/liter of L-glutamine (Pan Biotech, Batch: 8150713), 2% of PS solution, and 10 ng/ml of brain-derived neurotrophic factor (BDNF; Pan Biotech, Batch: H140108). Viable cells were counted in a Neubauer cytometer, using the trypan blue exclusion test. The cells were seeded at a density of 30,000 per well in 96-well plates precoated with poly-L-lysine (Corning Biocoat, Batch: 6614022) and were cultured at 37° C. in an air (95%)-$CO_2$ (5%) incubator. The medium was changed every 2 days. The cortical neurons were intoxicated with A-beta solutions (see below) after 11 days of culture.

Test Compounds and Amyloid-Beta 1-42 Exposure

The Amyloid-beta1-42 preparation was done following the procedure described by Callizot et al., 2013. Briefly, Amyloid-beta 1-42 peptide (Bachem, Batch: 1014012) was dissolved in the defined culture medium mentioned above, devoid of serum, at an initial concentration of 40 µmol/liter. This solution was agitated for 3 days at 37° C. in the dark and immediately used after being properly diluted in culture medium to the concentrations used.

Test compounds were solved in culture medium and then pre-incubated with primary cortical neurons for 1 hour before the Amyloid-beta 1-42 application. Amyloid-beta 1-42 preparation was added to a final concentration of 20 µM (including to ~2 µM of toxic oligomers measured by WB) diluted in control medium in presence of drugs. After 24 hours of intoxication, cells were fixed by a cold solution of ethanol (95%, Sigma, Batch: SZBD3080V) and acetic acid (5%, Sigma, Batch: SZBD1760V) for 5 min at −20° C. After permeabilization with 0.1% of saponin (Sigma, Batch: BCBJ8417V), cells were incubated for 2 h with mouse monoclonal antibody anti microtubule-associated-protein 2 (MAP-2; Sigma, Batch: 063M4802) at dilution of 1/400 in PBS (Pan biotech, Batch: 4831114) containing 1% foetal calf serum (Invitrogen, Batch: 41Q7218K) and 0.1% of saponin. This antibody was revealed with Alexa Fluor 488 goat anti-mouse IgG (Molecular probe, Batch: 1572559) at the dilution of 1/400 in PBS containing 1% foetal calf serum and 0.1% of saponin for 1 H at room temperature.

Analysis of Total Number of Neurons

The immunolabeled cultures were automatically examined with ImageXpress (Molecular device USA) at ×20 magnification. For each condition, 30 automatically fields per well (representing ~80% of the total surface of the well) from 3 wells were analyzed. The total number of neurons was automatically analyzed using Custom module editor (Molecular Devices, USA). Data were expressed in percentage of control conditions (no intoxication, no Amyloid-beta 1-42=100%) in order to express the A-beta 1-42 injury. All values were expressed as mean+/−SEM (s.e.mean) (n=3 wells per condition per culture).

1.10—In Vivo Mouse Model of Amyotrophic Lateral Sclerosis (ALS): SOD1-G93A Transgenic Mice Transgenic mice expressing mutated human SOD1-G93A transgenic (TG) mice (heterozygous TgN-SOD1-G93A-1Gur; Gurney et al. (1994) Science 264, 1772-1775) and 5 wild-type littermates were used for the experiments. G93A SOD1 mice were bred by Charles River Germany by mating hemizygous TG males (strain 002726M; B6SJL TG SOD1× G93A 1GUR/J, JAX) with WT females (strain 10012, JAX) obtained from JAX Laboratories USA. Animals were grouped as follows (the females and males were distributed equally to treatment groups i.e. each treatment group was strive to have equal numbers of males and females):

Transgenic G93A SOD1 mice
  12 transgenic G93A SOD1 mice treated with Vehicle QD (i.e. once a day) via oral gavage starting at 60 days of age and continuing until end-point
  12 transgenic G93A SOD1 mice treated with Compound 2 (1.5 mg/kg) BID (i.e. twice a day) via oral gavage starting at 60 days of age and continuing until end-point.
  12 transgenic G93A SOD1 mice treated with Compound 2 (3 mg/kg) QD via oral gavage starting at 60 days of age and continuing until end-point.
  12 transgenic G93A SOD1 mice treated with Compound 2 (3 mg/kg) QD in combination with riluzole (20 mg/kg) via oral gavage starting at 60 days of age and continuing until end-point.
  12 transgenic G93A SOD1 mice treated with Compound 2 (10 mg/kg) QD via oral gavage starting at 60 days of age and continuing until end-point.

Behavioral Testing

Rotarod test were performed before the dosing was started (baseline, day 60) and around day 75, 90, 105, and 120. Mice born within 2-4 days are pooled for rotarod testing. One day session includes a training trial of 5 min at 4 RPM on the rotarod apparatus (AccuScan Instruments, Columbus, USA). 30 min later, the animals are tested for 3 consecutive accelerating trials of 6 min with the speed changing from 0 to 40 RPM over 360 seconds and an inter-trial interval at least 30 min. The latency to fall from the rod is recorded. Mice remaining on the rod for more than 360 seconds are removed and their time scored as 360 seconds.

1.11—In Vivo Model of Charcot-Marie-Tooth 1A Disease: PMP-22 Overexpressing Transgenic Rat CMT1A transgenic rats were obtained from mating of male PMP-22 rats (Laboratory of Pr Nave, Max-Planck Institut für experimentelle Medizin, Göttingen, Germany) and female Sprague-Dawley rats (Elevage Janvier, France). Animals were housed and maintained at Key-Obs (Orléans, France). Animal procedures were conducted in strict adherence to the EU Directive of Sep. 22, 2010 (2010/63/UE).

Animals were grouped as follows (Only male animals were included in the experiments):
  8 transgenic rat treated with Vehicle QD via oral gavage starting at week 5 of age and continuing until end-point.
  8 transgenic rat treated with Compound 2 (1 mg/kg) QD via oral gavage starting at week 5 of age and continuing until end-point.
  8 transgenic rat treated with Compound 2 (3 mg/kg) QD via oral gavage starting at week 5 of age and continuing until end-point.

Behavioral Testing

Animals were tested in a random and blind manner for treatment and outcome measurements. Behavioral experiments and readouts of bar was performed and validated at Key-Obs facilities by the examiners who were blinded for the treatment. Bar test was performed on CMT1A rats after 3 weeks and 5 weeks of treatment. Bar test evaluated the muscular strength of the four paws and the equilibrium performances on a fixed rod. The rat was placed on its four paws on the middle of the wooden rod (diameter: 2.5 cm; length: 50 cm). The time spent on the bar (fall latency) in each trial and the number of falls were recorded. Five successive trials were performed (60 s max).

1.12—In Vitro Model of Leukodystrophy (PMD): Overexpression of Mutated PLP1 and DM20 in Human Cell Line One day before transfection, 293T cells were plated at 300,000 cells/mL. 293T cells were transfected with PLP1 and DM20 mutant constructs using Lipofectamine 2000 according to manufacturer's procedure. After transfection, cells were treated with molecules or left untreated. As a control, cells were transfected with native forms of the proteins. 48 h later, cellular lysates were harvested. Protein accumulation was assessed by western-blot.

1.13—In Vitro Model of Type 2 Diabetes: Min6 and INS1 Cell Lines

Cytoprotection from ER Stress

Cells were plated in 96 well plates at a density of $0.5 \cdot 10^6$ cells/mL for Min6 cell line, $0.4 \cdot 10^6$ cells/mL for INS1 cell line the day before the treatment.

ER stress was elicited by addition of 2.5 µg/mL tunicamycin (Sigma Aldrich) together with phosphatases inhibitors. Media were changed 6 h later with fresh media and the cytoprotection was maintained by the addition of phosphatases inhibitors.

Cell viability was assessed by measuring the reduction of WST-8 into formazan using Cell Counting Kit-8 (Sigma) according to the supplier's recommendation, 72 h after tunicamycin treatment.

Protection Against Accumulation of Misfold Prone Insulin$^{Akita}$

Min6 cells were nucleofected with Insulin$^{Akita}$ a mutant constructs and seeded in 96 well-plates at 300,000 cells/mL and 24 h later, cells were treated with molecules or left untreated. As a control, cells were nucleofected with non-relevant plasmid. 6 days later, a selective agent was added (G418).

Cell viability was assessed by measuring the reduction of WST-8 into formazan using Cell Counting Kit-8 (Sigma) according to the supplier's recommendation, 9 days after treatment.

1.14—In Vitro Inflammation/Infection Disease Model: Poly I:C Induced Mouse Embryonic Fibroblasts Experimental Protocols Mouse Embryonic Fibroblasts (MEFs) were lipofected with poly I:C and treated with two concentrations of compounds of the invention (25 µM) for 6 h. After 6 h of culture, eIF2alpha-phosphorylation (eIF2α-P) and PPP1R15A (GADD34) expression was monitored by western blotting, while type-I Interferon (IFN)-beta production was quantified in culture supernatants by ELISA. Control (nt) and poly I:C/DMSO are respectively negative and positive controls.

Poly I:C (polyinosinic:polycytidylic acid or polyinosinic-polycytidylic acid sodium salt) is an immunostimulant used to simulate viral infections. Poly I:C which is structurally similar to double-stranded RNA, is known to interact with toll-like receptor 3 which is expressed in the intracellular compartments of B-cells and dendritic cells. Guanabenz (25 µM) was used as reference inhibitory compound.

Cell Culture

MEFs were cultured in DMEM, 10% FCS (HyClone, Perbio), 100 units/ml penicillin, 100 µg/ml streptomycin, 2 mM glutamine, 1×MEM non-essential amino acids and 50 µM 2-mercaptoethanol. MEFS were treated for the indicated time with 10 µg/ml poly I:C (InvivoGen) in combination with lipofectamine 2000 (Invitrogen).

Immunoblotting

Cells were lysed in 1% Triton X-100, 50 mM Hepes, 10 mM NaCl, 2.5 mM $MgCl_2$, 2 mM EDTA, 10% glycerol, supplemented with Complete Mini Protease Inhibitor Cocktail Tablets (Roche). Protein quantification was performed using the BCA Protein Assay (Pierce). 25-50 µg of Triton X-100-soluble material was loaded on 2%-12% gradient or 8% SDS-PAGE before immunoblotting and chemi-luminescence detection (SuperSignal West Pico Chemi-luminescent Substrate, Pierce). Rabbit polyclonal antibodies recognizing GADD34 (C-19) were from Santa Cruz Biotechnology and anti-eIF2alpha[$pS^{52}$] were from Invitrogen.

Elisa

IFN-beta quantification in culture supernatant was performed using the Mouse Interferon Beta ELISA kit (PBL Interferon Source) according to manufacturer instructions.

1.15—In Vivo Retinal Ciliopathies/Retinitis Pigmentosa Symptoms: BBS12 Knock-Out Mice Generation of Knockout Mice and Animal Husbandry Bbs12$^{-/-}$/J mice were kept on a C57BL/6 genetic background (Mockel et al., 2012 J. Biol. Chem. 287 pp 37483-494). Mice were kept and bred in humidity- and temperature-controlled rooms on a 12 hour light/dark cycle with free access to normal chow and water. Bbs12$^{-/-}$ total knock-out mice were identified by genotyping through Polymerase Chain Reaction (PCR) using KAPA Mouse Genotyping Kit (Catalog # KK7302, Kapa Biosystems, Woburn, Mass., USA).

Reagents for Intra-Vitreal Injection

The solution used for intravitreal injection was prepared under sterile condition. 1.25 mM of compound 2 and 100 mM Valproic acid (VPA) stock solutions were then diluted into PBS, pH6 to obtain compound 2 (2.5 µM)+VPA (0.2 mM) and compound 2 (2.5 µM) solutions. Valproic acid was sourced (Catalog #4543, Sigma-Aldrich).

Intra-Vitreal Injection

Bbs12$^{-/-}$ mice retinal phenotypes and mechanism were published (Mockel et al., 2012). At postnatal day 14-16 mice were injected intravitreally. The operation was performed under surgical microscope. Mice were anesthetized with isoflurane. Pupils of mice were dilated with 0.3% Atropine eye drops (Alcon). A 33-gauge needle connected to a repeating dispenser (Hamilton Bonaduz AG, Bonaduz, Switzerland) was inserted into the vitreous cavity from the limbus. The location of needle was monitored through the microscope. 1 µl treatment solution was injected into the left eye of mice, and 1 µl PBS, pH6 was administered into the right eye as control. Mice with vitreous hemorrhage or retinal damage were excluded from analysis.

Electroretinograms

Electroretinograms (ERGs) were performed two weeks after intravitreal injection using the HMsERG system (Ocuscience®, Kansas City, Mo., USA). Mice were dark-adapted overnight and then anesthetized by intraperitoneal injection of domitor (7.6 µg/g body weight) and ketamine (760 µg/g body weight). Pupils were dilated as described above. The experiments were carried out in dim red light (catalog # R125IRR, Philips, Suresnes, France). ERGs standard procedure was used according to manufacturer's protocol (Ocuscience®, Kansas City, Mo., USA). Briefly, the protocol consisted in recording a dark-adapted ERG (scotopic ERG) after photonic stimuli with intensities ranging from 0.1 to 25 cd·s/$m^2$. ERG results were amplified and captured digitally by ERG View system 4.3 (Xenotec, Ocuscience®, Kansas City, Mo., USA). The a-wave and b-wave of scotopic responses were then measured.

Transmission Electron Microscopy

The samples were fixed by immersion in 2.5% Glutaraldehyde and 2.5% Para formaldehyde in Cacodylate buffer (0.1M, pH 7.4), and post fixed in 1% osmium tetroxide in 0.1M Cacodylate buffer for 1 hour at 4° C. and dehydrated through graded alcohol (50, 70, 90, 100%) and propylene oxide for 30 minutes each. Samples were embedded in Epon™ 812 (Sigma-Aldrich, Saint-Louis, Mo., USA). Semi-thin sections were cut at 2 µm with an ultra-microtome (Leica Ultracut UCT, Leica Biosystems, Wetzlar, Germany) and stained with toluidine blue, and histologically analyzed by light microscopy. Ultrathin sections were cut at 70 nm and contrasted with uranyl acetate and lead citrate and examined at 70 kv with a Morgagni 268D electron microscope. Images were captured digitally by Mega View III camera (Soft Imaging System).

1.16—Hypoxia-Induced Apoptosis in Cultured Neonatal Rat Cardiomyocytes

Cell Culture

Primary cultures of neonatal rat cardiomyocytes were obtained from the ventricles of 1-day-old Sprague Dawley rats (Janvier, France). The rats were euthanized and their hearts excised. Hearts cut into small pieces (1-2 $mm^3$) and enzymatically digested using the Neonatal Heart Dissociation Kit rat and the gentleMACS™ Dissociator (Miltenyi-Biotec, Germany). After dissociation, the homogenates were filtered (70 µm) to obtain a single-cell suspension. Isolated cells were collected by centrifugation and resuspended in Dulbecco's Modified Eagle's Medium (DMEM) containing 10% horse serum (HS), 5% fetal bovine serum (FBS) and 1% penicillin/streptomycin. Cultures were enriched with myocytes by pre-plating for 90 min to deplete the population of non-myocytes. Non-attached cells were plated onto 6- or 96-well plates at an appropriate cell density. The cells were cultured at 37° C. in 95% air/5% $CO_2$ for 24 h. Then the culture medium was exchanged with fresh DMEM containing 1% FBS and different concentrations of test compound thirty minutes before incubation in a normal or a hypoxic ($N_2$/$CO_2$, 95%/5%; 0.3% $O_2$) culture chamber.

Treatment with Test Compound

Purified neonatal rat cardiomyocytes were seeded in a 96-well plate at $10^6$ cells/2 mL for flow cytometry experiments.

After 24 hours, the cardiomyocytes were treated with different concentrations of test compound in culture medium with 0.1% DMSO. The positive controls cells were treated with culture medium (0.1% DMSO). Thirty minutes after starting the treatments, the cells were incubated in the hypoxic culture chamber ($N_2/CO_2$, 95%/5%; final measured $O_2$: 0.3%) for 36 hours.

The negative controls cells were left in normoxic conditions at 37° C. with culture medium (1% FBS, 0.1% DMSO) for the same time periods.

Apoptotic Cell Measurement

At the end of the treatment period, flow cytometry were performed to measure the amount of apoptotic cells. The Annexin V-fluorescein isothiocyanate (FITC) apoptosis detection kit from Miltenyi was used. Cells were washed twice with PBS and re-suspended in binding buffer. FITC-Annexin V and propidium iodide were added according to the manufacturer's protocol. The mixture was incubated for 15 min in the dark at room temperature, and cellular fluorescence was then measured by FACS scan flow cytometry.

2—Results 2.1—Cytoprotection & Compound Selectivity

The results of the different assays ran with selected compounds of the invention are shown below in Table 1.

Figure 1:
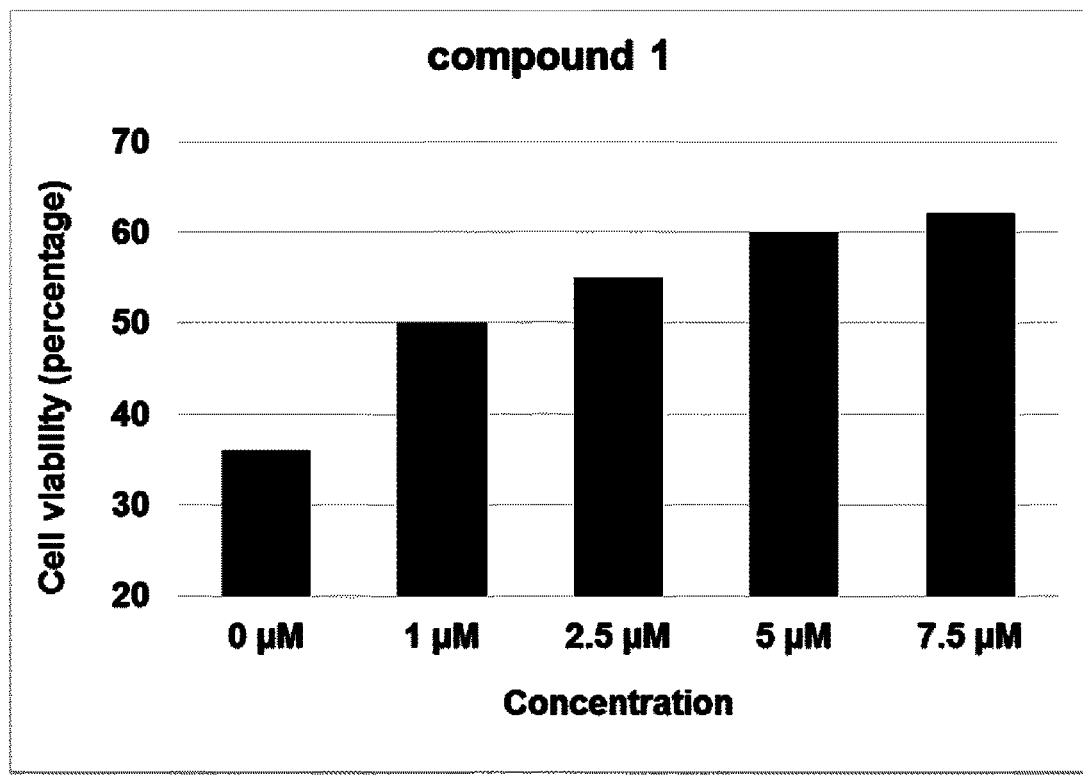
FIG. 1 shows dose dependent protection of Hela cells by compound 1 of the invention from ER stress induced by 6 hour exposure to tunicamycin.

As example, FIG. 1 represents the cytoprotective effect of compound 1 after the stress induced by an exposure of tunicamycin.

TABLE 1

| Compound No | Cyto-protection from ER stress compared to guanabenz | Translation inhibition in non-stressed cells | Translation recovery after Tunicamycin treatment | Functional adrenergic alpha2 receptor assay |
|---|---|---|---|---|
| 1 | ++ | no effect | prolongs | EC50 > 33.3 μM |
| 2 | ++ | no effect | prolongs | EC50 > 33.3 μM |
| 3 | ++ | no effect | | |
| 4 | + | | | |
| 5 | + | | | |
| 6 | + | no effect | | |
| 7 | ++ | no effect | | EC50 > 33.3 μM |
| 8 | ++ | no effect | | |
| 9 | − | | | |
| 10 | + | | | |
| 11 | + | | | |

2.2—Multiple Sclerosis

Figure 2:
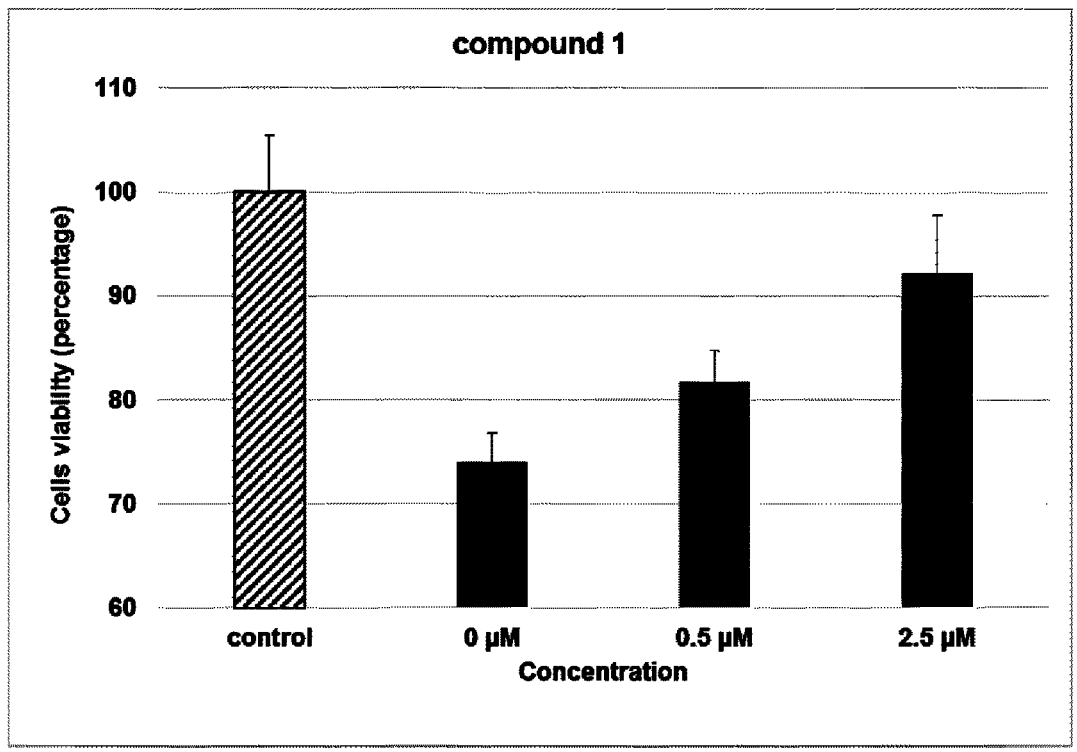
FIG. 2 shows dose dependent protection of interferon-gamma injured rat oligodendrocytes by compound 1 of the invention.

FIG. 2 shows dose dependent protection of interferon-gamma injured rat oligodendrocytes by compound 1 of the invention.

These data show that the compounds of this invention are promising effective treatment of Multiple Sclerosis.

2.3—Parkinson's Disease (PD)

Figure 3:
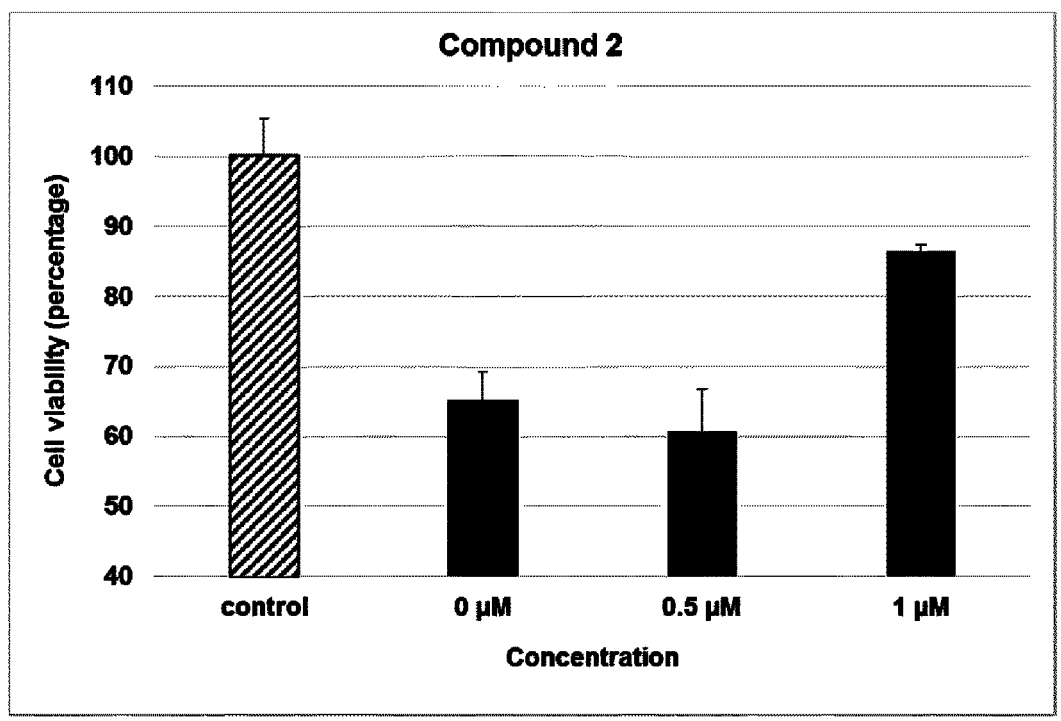
FIG. 3 shows dose dependent protection of rotenone injured primary mesencephalic rat neurons by compound 2 of the invention.

FIG. 3 shows dose dependent protection of rotenone injured primary mesencephalic rat neurons by compound 2 of the invention.

These data show that the compounds of this invention are promising effective treatment of synucleopathies, and more specifically Parkinson's disease.

2.4—Alzheimer Disease (AD) & Amyloidosis

Figure 4:
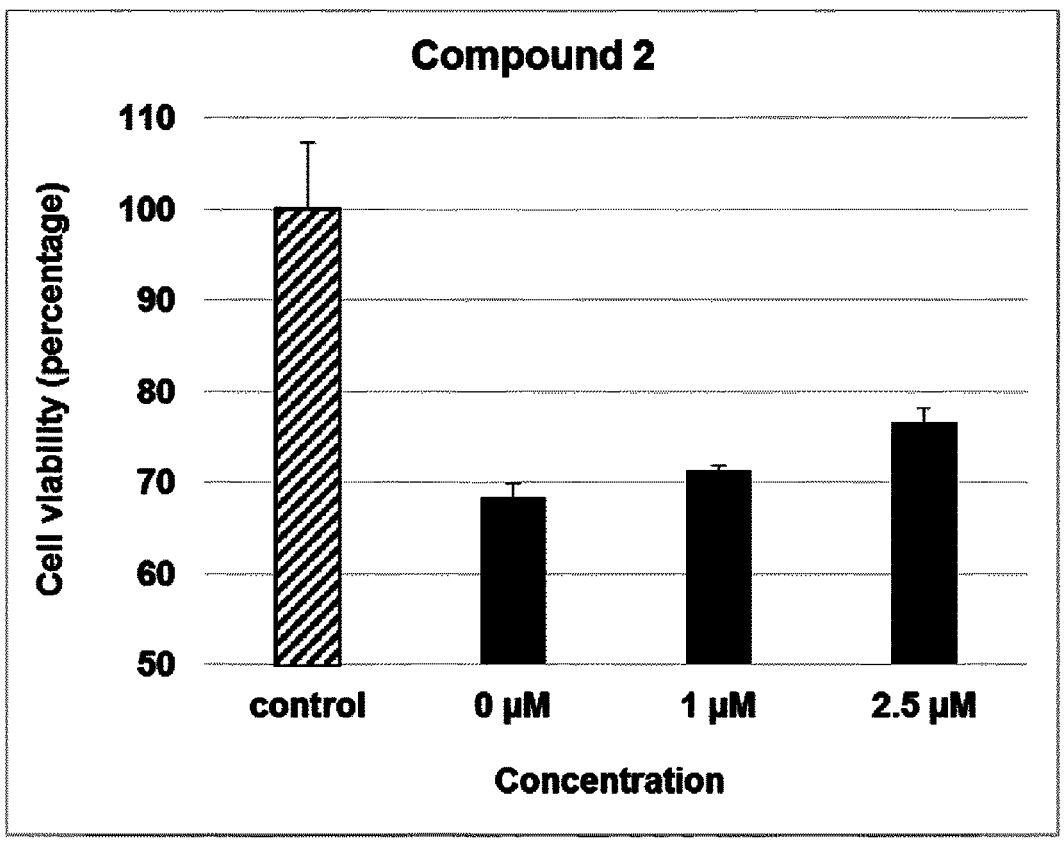
FIG. 4 shows dose dependent protection of amyloid-beta 1-42 injured primary cortical rat neurons by compound 2 of the invention.

FIG. 4 shows dose dependent protection of amyloid-beta 1-42 injured primary cortical rat neurons by compound 2 of the invention.

These data show that the compounds of this invention are promising effective treatment of Amyloidosis and more specifically Alzheimer disease.

2.5—Amyotrophic Lateral Sclerosis (ALS)

Figure 5:
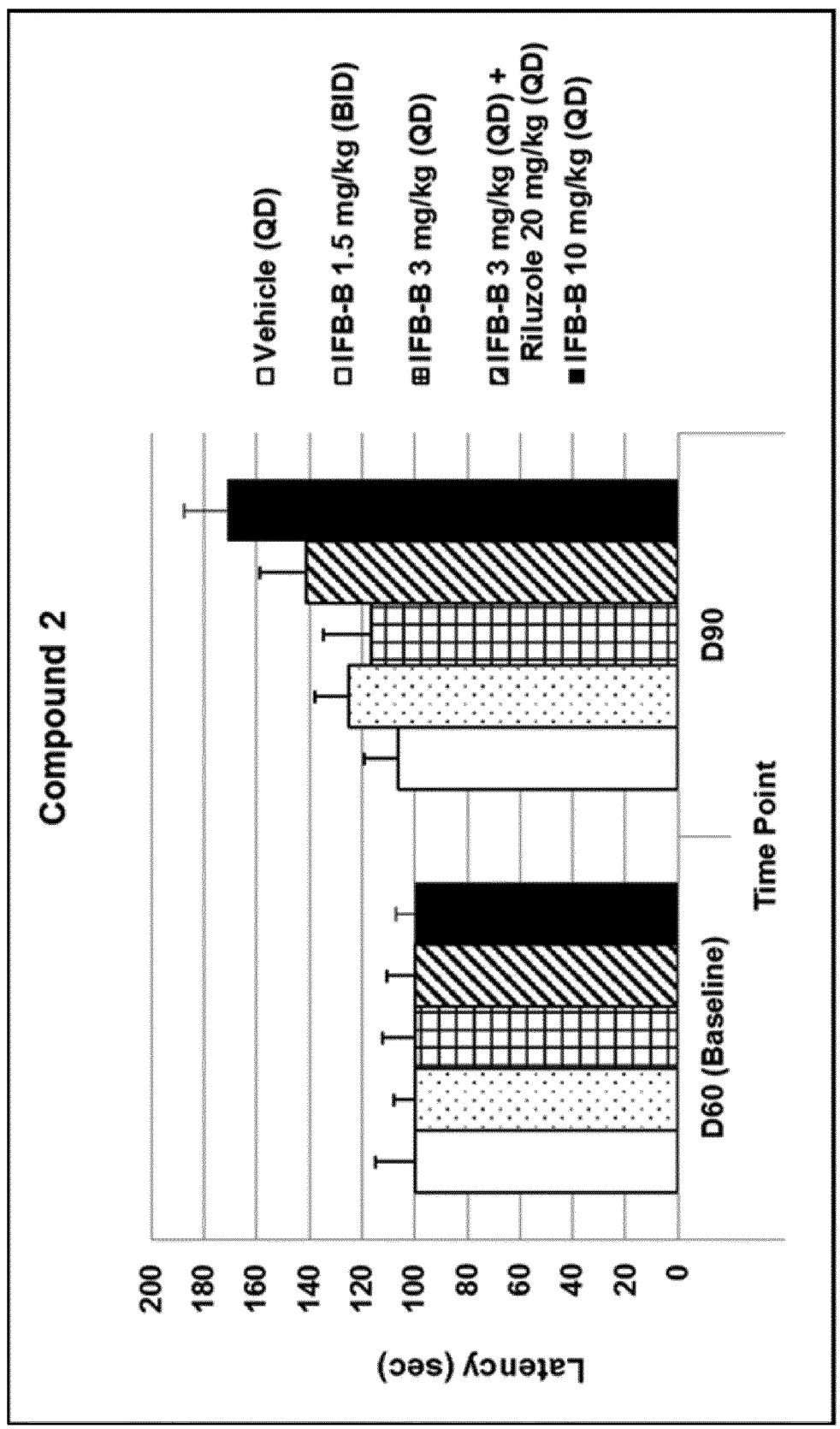
FIG. 5 shows the ability of compound 2 at different concentration and regimen to prevent motor defects of ALS in mutant SOD1 mice.

FIG. 5 represents the results of rotarod test at day 90 of transgenic SOD1 G93A mice with compound 2 of the invention.

These data show that the compounds of this invention, specifically compounds 1 and 2, rescue motor deficit of transgenic mice and are promising effective treatment of ALS.

2.6—Charcot-Marie-Tooth 1A (CMT-1A)

FIG. 6 represents the results of bar test at weeks 3 and 5 of transgenic rat overexpressing PMP22 treated with compound 2 of the invention.

These data show that the compounds of this invention, specifically compounds 1 and 2, rescue motor deficit of transgenic rat overexpressing PMP22 and are promising effective treatment of demyelinating disorders like CMT, more specifically CMT1A and CMT1B.

2.7—Leukodystrophy: Pelizaeus-Merzbacher Disease (PMD),

T181P and L223P mutations in PLP1 and DM20 proteins have been described to cause a severe phenotype of Pelizaeus-Merzbacher disease (Strautnieks et al. 1992, Am. J. Hum. Genet. 51 (4): 871-878; Gow and Lazzarini, 1996 Nat Genet. 13(4):422-8).

The Compound 1 of the invention (5 microM) is able to prevent the accumulation of T181P mutated DM20 protein expressed in Human 293T cell (FIG. 7).

These data show that the compounds of this invention, specifically compounds 1 and 2, are promising effective treatment of demyelinating disorders like leukodystrophies, more specifically PMD.

2.8—Type 2 Diabetes

FIG. 8 represents the results of over expression of pre-pro-insulin bearing Akita mutation in Min6 cells with compound 6 of the invention.

The Compound 1 and compound 6 at different concentrations prevent Min6 insulinoma cell death associated with accumulation of misfolded protein induced by 6 hour exposure to tunicamycin (FIG. 9)

The compound 1 and compound 6 at different concentrations prevent INS1 insulinoma cell death associated with accumulation of misfolded protein induced by 6 hour exposure to tunicamycin. (FIG. 10).

These data show that the compounds of the invention are promising effective treatment of pre-diabetes and diabetes, preferably type 2 pre-diabetes and type 2 diabetes.

2.9—Retinal Ciliopathies/Bardet Biedl Syndrome

The compound 2 is able to protect photoreceptors against apoptosis and preserves light detection (FIG. 11) and to decrease protein load in the Endoplasmic Reticulum (FIG. 12) in BBS12−/− mice. These results show an increased ERG response when treated with the Compound 2 and Valprolc acid (VPA) combination or with compound 2 alone in the Bbs12−/− mice (FIG. 11). FIG. 12 shows a representative transmitted electron microscopy picture of ER of the photoreceptors of BBS12−/− mouse in response to the indicated administrated treatment or genotype. Dilatation is observed when PBS only is injected (left) whereas Compound 2 (2.5 microM) in combination with VPA (valproic acid) (0.2 mM) are able to decrease this dilatation after one single intra-vitreal injection.

These data show that the compounds of this invention in association with a compound increasing the expression and/or the activity of BIP protein, such as Valproic acid, are promising effective treatment of retinal ciliopathies such as Bardet-Biedl syndrome and retinitis pigmentosa.

Although not tested, we hypothesized that this treatment might also be helping in reducing other forms of cellular stress like the photonic stress.

2.10—Infection-Related or Non-Infectious Inflammatory Conditions

Normal response of MEFs to poly I:C is characterized by PPP1R15A expression, increase in eIF2alpha-P (variable in time and related to the levels PPP1R15A expression) mediated by PKR activation and type-I IFN production (range 500 to 700 µg/ml). Knock out PPP1R15A−/− MEFs are unable to produce this cytokine in response to poly I:C.

The potency of compounds of the invention to inhibit PPP1R15A was evaluated by measuring the increase of eIF2alpha phosphorylation, the decrease of PPP1R15A expression due to its own pharmacological inhibition resulting in general protein synthesis inhibition and type-I IFN production.

The evaluated compounds of the invention were found efficient at 25 µM to increase eIF2alpha phosphorylation, to decrease of PPP1R15A expression and to prevent type-I IFN production. As example, FIG. 13 shows the ability of compounds 1, 6 and 8 (at 25 microM) to prevent type-I IFN production by mouse embryonic fibroblasts lipofected with poly I:C.

These data show that the compounds of this invention are promising effective treatment of infection-related or non-infectious inflammatory conditions.

2.11—Cardiac Ischemia

The compound 2 of the invention protects cultured neonatal rat cardiomyocytes from hypoxia-induced apoptosis (FIG. 14). These data show that the compounds of this invention are promising effective treatment of ischemia, specifically cardiac ischemia.

Various modifications and variations of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant fields are intended to be covered by the present invention.

The invention claimed is:

1. A method for treating a disorder selected from the group consisting of leukodystrophies, inflammatory conditions, cystic fibrosis and oculo-pharyngeal muscular dystrophy (OPMD), wherein the inflammatory conditions are selected from the group consisting of sepsis and systemic inflammatory response syndrome (SIRS), comprising administering to a patient in need thereof, a compound of formula (I), or a pharmaceutically acceptable salt thereof,

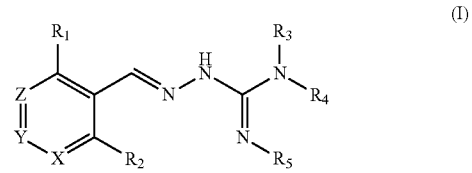

wherein:
$R_1$ is alkyl, O-alkyl, Cl, F or Br;
$R_2$ is H or F;
$R_3$ is H or alkyl;
$R_4$ is H or $C(O)R_6$;
$R_5$ is H;
or $R_4$ and $R_5$ are linked to form a 5 to 6 membered saturated or unsaturated heterocyclic group optionally comprising 1 or 2 heteroatoms such as N, in addition to the N atoms to which $R_4$ and $R_5$ are bound, and where said heterocyclic group is optionally substituted with one or more $R_{10}$ groups;
$R_6$ is selected from the group consisting of $R_7$, $OR_7$ and $NR_8R_9$;
$R_7$, $R_8$ and $R_9$ are each independently selected from the group consisting of alkyl, cycloalkyl, aralkyl, cycloalkenyl, heterocyclyl and aryl, each of which is optionally substituted with one or more $R_{10}$ groups;
each $R_{10}$ is independently selected from the group consisting of halogen, OH, =O, CN, COO-alkyl, aralkyl, $SO_2$-alkyl, $SO_2$-aryl, COOH, CO-alkyl, CO-aryl, $NH_2$, NH-alkyl, $N(alkyl)_2$, $CF_3$, alkyl and alkoxy;
X and Z are each independently $CR_{11}$, and Y is $CR_{11}$ or N; and
$R_{11}$ is H, alkyl or F.

2. The method according to claim 1 wherein
$R_7$, $R_8$ and $R_9$ are each independently alkyl; and
$R_{11}$ is H, or F.

3. The method according to claim 1 wherein $R_1$ is Cl, Br, Me, or F.

4. The method according to claim 1 wherein $R_2$ is H.

5. The method according to claim 1 wherein Y is $CR_{11}$.

6. The method according to claim 1 wherein $R_3$ and $R_4$ are both H.

7. The method according to claim 1 wherein $R_3$ is H and $R_4$ is $C(O)R_6$, wherein $R_6$ is Me or OMe.

8. The method according to claim 1 wherein said compound is selected from the group consisting of:

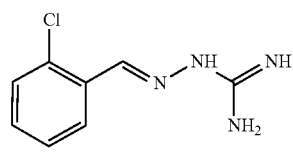

Compound 1

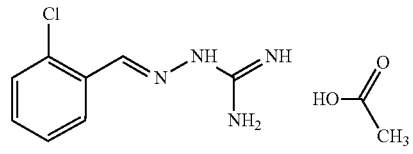

Compound 2

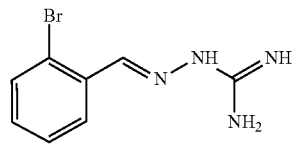

Compound 3

-continued

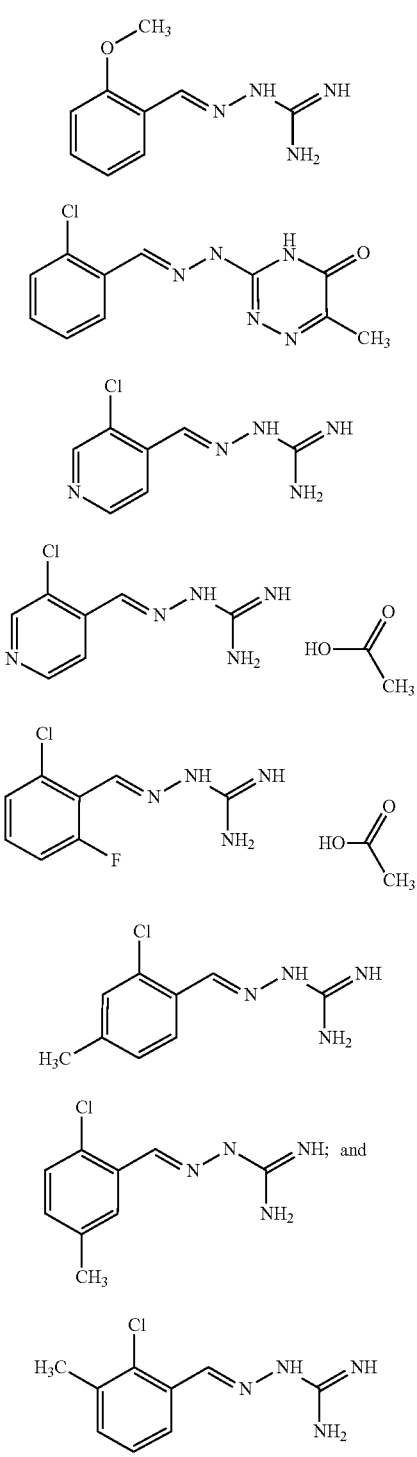

or acceptable salt thereof.

9. The method according to claim 1 wherein the compound is selected from the group consisting of:

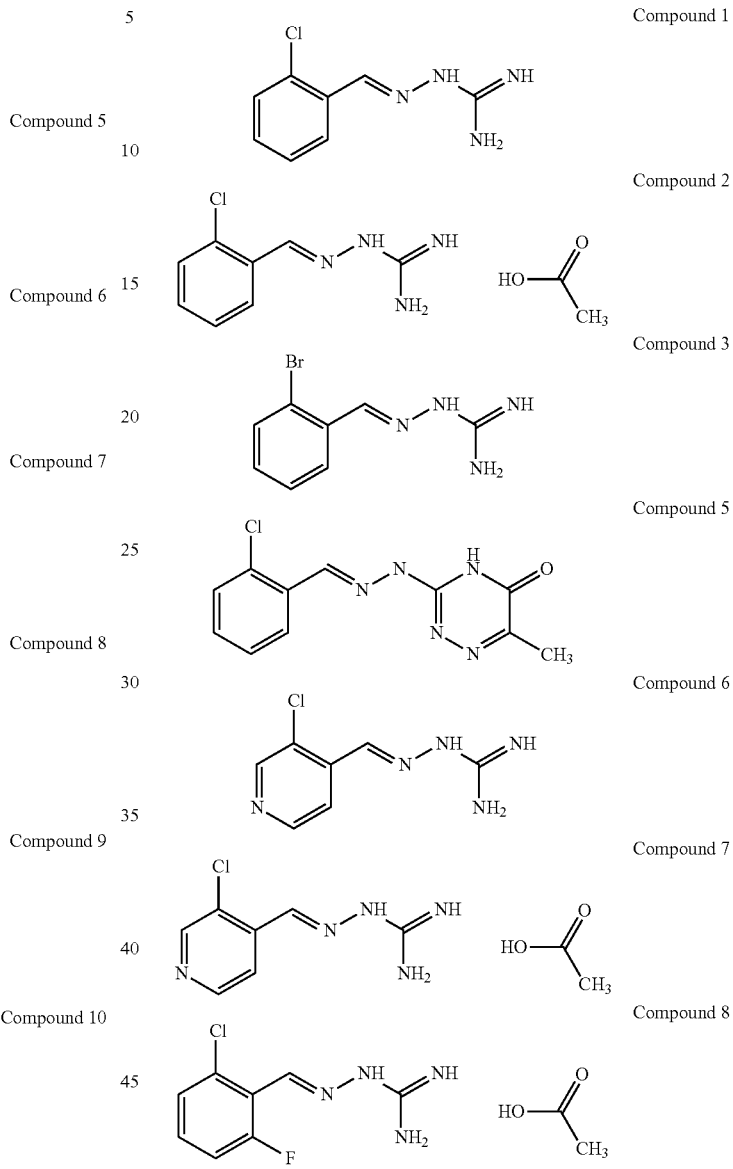

or acceptable salt thereof.

10. The method according to claim 9 wherein the compound is compound 1 or a pharmaceutically acceptable salt thereof.

11. The method according to claim 1 wherein the disorder is a leukodystrophy.

12. The method according to claim 11 wherein the leukodystrophy disorder is Pelizaeus-Merzbacher disease.

* * * * *